United States Patent
Hogue et al.

(10) Patent No.: US 6,745,204 B1
(45) Date of Patent: Jun. 1, 2004

(54) SYSTEM FOR ELECTRONICALLY MANAGING, FINDING, AND/OR DISPLAYING BIOMOLECULAR INTERACTIONS

(75) Inventors: Christopher Hogue, Oakville (CA); Gary Bader, North York (CA)

(73) Assignee: Mount Sinai Hospital, Toronto (CA)

( * ) Notice: Subject to any disclaimer, the term of this patent is extended or adjusted under 35 U.S.C. 154(b) by 0 days.

(21) Appl. No.: 09/503,614

(22) Filed: Feb. 11, 2000

Related U.S. Application Data
(60) Provisional application No. 60/119,850, filed on Feb. 12, 1999.

(51) Int. Cl.[7] .............................................. G06F 17/00
(52) U.S. Cl. ................................................... 707/104.1
(58) Field of Search .............................. 707/1–6, 9, 10, 707/100, 102–104.1, 200, 201, 203, 204, 500–501.1, 514, 515; 709/200–203, 217–219; 345/418–420, 440, 700, 810, 853, 965–968; 715/500–501.1, 514, 515

(56) References Cited

U.S. PATENT DOCUMENTS

| | | | | |
|---|---|---|---|---|
| 4,980,840 A | * | 12/1990 | Yin et al. ................... | 345/467 |
| 5,265,247 A | * | 11/1993 | Wienck et al. .............. | 366/6 |
| 5,497,319 A | * | 3/1996 | Chong et al. ................ | 704/10 |
| 5,787,279 A | * | 7/1998 | Rigoutsos ................... | 707/104.1 |
| 5,843,665 A | * | 12/1998 | Hawkins et al. ............ | 435/6 |
| 5,969,123 A | * | 10/1999 | Holtzman ................... | 536/22.1 |
| 5,980,096 A | * | 11/1999 | Thalhammer-Reyero ... | 703/13 |
| 6,092,080 A | * | 7/2000 | Gustman ..................... | 707/102 |
| 6,133,419 A | * | 10/2000 | Braselmann ............... | 435/320.1 |
| 6,182,129 B1 | * | 1/2001 | Rowe et al. ................ | 707/501.1 |
| 6,311,189 B1 | * | 10/2001 | deVries et al. ............. | 707/102 |
| 6,352,834 B1 | * | 3/2002 | Dreicer et al. .............. | 435/7.1 |
| 6,353,026 B1 | * | 3/2002 | Serhan ....................... | 514/558 |
| 2001/0028649 A1 | * | 10/2001 | Pogossiants et al. ........ | 370/389 |
| 2001/0056504 A1 | * | 12/2001 | Kuznetsov ................... | 709/310 |

FOREIGN PATENT DOCUMENTS

| | | |
|---|---|---|
| WO | WO 97/47763 | 12/1997 |
| WO | WO 98/23781 | 6/1998 |
| WO | WO 99/58719 | 11/1999 |

OTHER PUBLICATIONS

Midas Database System, Ferrin, Thomas E.; Huang, Conrad C.; Jarvis, Laurie R.; Langridge, Robert, Journal of Molecular Graphics, v. 6, n. 1, Mar. 1988, pp. 2–12.*

Midas Display System, Ferrin, Thomas E.; Huang, Conrad C.; Jarvis, Laurie R.; Langridge, Robert, Journal of Molecular Graphics, v. 6, n. 1, Mar. 1988, pp. 13–27, 36–40.*

Hogue et al. "A dynamic look at structures: WWW–Entrez and the Molecular Modeling Database," *TIBS*, vol. 21, No. 6 (Jun. 1996): pp. 226–229. XP004050897.

Hogue. "Cn3D: a new generation of three dimensional molecular structure viewer," *TIBS*, vol. 22, No. 8 (Aug. 1997): pp. 314–316. XP004085819.

Altschul, S.F. et al. (1997) Nucleic.Acids.Res., 25, 3389–3402.

(List continued on next page.)

Primary Examiner—Greta Robinson
Assistant Examiner—Harold E. Dodds, Jr.
(74) Attorney, Agent, or Firm—Merchant & Gould, P.C.

(57) ABSTRACT

A system for electronically, managing, finding, and/or visualizing biomolecular interactions is described. A computer-implemented system of the invention has a database having a plurality of records. Each record contains a reference biomolecular interaction defined by a chemical graph and descriptive information from an external database. The information correlates the biomolecular interactions to records in the external batabase. The system has a user interface allowing a user to selectively view information regarding a biomolecular interaction.

26 Claims, 14 Drawing Sheets

OTHER PUBLICATIONS

Bairoch, A. & Apweiler, R. (1999) Nucleic.Acids.Res., 27, 49–54.

Benson, D.A. et al. (1999) GenBank. Nucleic.Acids. Res., 27, 12–17.

Bernstein, F.C. et al. (1978) Arch.Biochem.Biophys., 185, 584–591.

Weininger, D. (1988) J.Chem.Inf.Comput.Sci., 28, 31–36.

Schuler, G.D., Epstein, J.A., Ohkawa, H. & Kans, J.A. (1996) Methods Enzymol., 266, 141–162.

Gasteiger, J. (1996) Chemical Information in 3D–Space. J.Chem.Inf.Comput.Sci., 36, 1030–1037.

Higgins, D.G., Thompson, J.D. & Gibson, T.J. (1996) Methods Enzymol., 266, 383–402.

Hogue, C.W., Ohkawa, H. & Bryant, S.H. (1996) Trends. Biochem.Sci., 21, 226–229.

Stoesser, G., Tuli, M.A., Lopez, R. & Sterk, P. (1999) Nucleic.Acids.Res., 27, 18–24.

Kans, J.A. & Ouellette, B.F. (1998) In Baxevanis, A.D. & Ouellette, B.F. (eds), Bioinformatics. John Wiley & Sons Toronto pp. 319–353.

Marcotte, E.M., Pellegrini, M., Ng, H.L., Rice, D.W., Yeates, T.O. & Eisenberg, D. (1999) Science, 285, 751–753.

Mendelsohn, A.R. & Brent, R. (1999) Science, 284, 1948–1950.

Mohr, E., Horn, F., Janody, F., Sanchez, C., Pillet, V., Bellon, B., Roder, L. & Jacq, B. (1998) Nucleic.Acids.Res., 26, 89–93.

Sugawara, H., Miyazaki, S., Gojobori, T. & Tateno, Y. (1999) Nucleic.Acids.Res., 27, 25–28.

Ostell, J. & Kans, J.A. (1998) Bioinformatics. John Wiley & Sons pp. 121–144.

Bader, G. and C.W.V. Hogue. Bioinformatics vol. 16 No. 5 p. 465, 2000.

Marchler–Bauer, A. et al. Nucleic Acids Research, 1999, vol. 27, No. 1., p. 240.

Abola, E.E. et al. The protein Data Bank in The Role of Data on Scientific Progress, P.S. Glaeser(ed) Elsevier Science Publishers, 1985.

Ferrin, T. E. et al., "The MIDAS database system", *J. Mol. Graphics*, 6(1):2–12 (Mar. 1988).

Ferrin, T.E. et al., "The MIDAS database system", *J. Mol. Graphics*, 6(1):13–27 (Mar. 1988).

* cited by examiner

BIND
Major Subsystem Overview

SYSTEM FOR ELECTRONICALLY MANAGING, FINDING, AND/OR DISPLAYING BIOMOLECULAR INTERACTIONS

This application claims the benefit of provisional application No. 60/119,850, filed Feb. 12, 1999.

A portion of the disclosure of this patent document contains material which is subject to copyright protection. The copyright owner has no objection to the facsimile reproduction by any one of the patent disclosure, as it appears in the Patent and Trademark files or records, but otherwise reserves all copyright rights whatsoever.

REFERENCE TO A COMPUTER PROGRAM LISTING APPENDIX

The present application includes and incorporates by reference a computer sequence listing appendix on a single compact disc and its duplicate, each compact disc was created on Oct. 23, 2003 and includes the files Appendix A.doc (96 kB) and Appendix B.doc (160 kB).

FIELD OF THE INVENTION

The invention relates to a system, methods and products for managing, finding, and/or displaying biomolecular interactions.

BACKGROUND OF THE INVENTION

Technological advances and mounting interest have pushed proteins into the scientific spotlight. This growing field encompasses the study of proteins, both in structure and in function, contained in a proteome—the protein equivalent of a genome. Because of increased interest and technique automation (Mendelsohn et al., 1999), the rate of proteomic data production is growing in a similar fashion as that of genomics a decade ago. For example, mass spectrometers, gene chips, and two-hybrid systems have made cellular signaling pathway mapping faster and easier and consequently these are becoming large producers of data. Protein-protein interaction and more general biomolecule-biomolecule (protein-DNA, protein-RNA, protein-small molecule, etc.) interaction information is being generated and recorded in the literature. Lessons from the genomic era have taught us that large amounts of related data recorded in scientific journals soon becomes unmanageable. A well designed common data specification based on a model of the biological information is therefore required to describe and store biomolecular interaction data.

SUMMARY OF THE INVENTION

The present inventors have designed a data specification for the storage and management of biomolecular interaction and biochemical pathway data that possesses the following properties:

1. It describes the full complexity of the biological data, from simple binary interactions to large-scale molecular complexes and networks of pathways and interactions. It stores protein, DNA, RNA, and other molecules in full atomic detail, since character based sequence abstractions of biomolecules often miss important chemical features, such as methylation on DNA. This allows as much data as possible to be stored for scientific use in electronic form rather than in print.

2. It is easily computable. A computer can easily read, write, and traverse the specification. This facilitates maintenance of a database of such information, creation of advanced queries and querying tools and development of computer programs that use the information for data visualization, data mining, and visual data entry.

3. It is platform and database independent. Tools written for one platform can read data created on another platform directly. It handles the data structure without modification as well.

4. It is succinct and easy for humans to understand. Field to data correspondence is very clear and a human readable format of the specification is available.

The data structure was designed for a database referred to herein as "BIND" (Biomolecular Interaction Network Database). The data structure is written in a data specification language called Abstract Syntax Notation. 1 (ASN.1, also known as X.208 or ISO-8824) The U.S. National Center for Biotechnology Information (NCBI) uses ASN.1 to describe and store all of its biological and publication data and all of GenBank, MMDB and PubMed (Ostell and Kans, 1998). BIND inherits the NCBI data model, which provides a solid foundation for the BIND data specification through the use of mature NCBI data types that describe sequence, 3D structure, and publication reference information.

Although the specification is written in ASN.1, it is not restricted to this syntax. The data structures can be readily translated to other common data specification languages such as CORBA IDL (Object Management Group, 1996) or XML if the need arises. Aside from ASN.1, no other biological data specification is sufficiently rich in mature data types to use as a foundation for BIND without first building and testing those base data types.

The BIND data specification represents complex cellular pathway information efficiently in a computer. BIND defines three main data types: interactions, molecular complexes, and pathways. Each of these objects is composed of various component and descriptor objects that are either defined in the specification proper or inherited from the NCBI ASN.1 data specifications. For example, an interaction record contains, among other data objects, two BIND-objects. A BIND-object describes a molecule of any type and is itself defined using simpler sub-objects. Normally, a BIND-object describing a biopolymer sequence will store a simple link to a sequence database, such as GenBank (Benson et al., 1999). If, however, the sequence is not present in a public database, it can be fully represented using an embedded NCBI-Bioseq object. The NCBI-Bioseq object is how NCBI stores all of the sequences in GenBank and is a mature data structure. BIND also inherits the NCBI taxonomy model (also used and supported by EMBL, DDBJ and Swiss-Prot) and data, via an inherited NCBI-BioSource, and is designed so that interactions can be both inter- and intra-organismal. Sequence, structure, publication, taxonomy and small molecule databases provide a strong foundation for BIND.

Broadly stated, the present invention contemplates a system for electronically managing, finding, and/or visualizing biomolecular interactions comprising a computer system including at least one computer receiving data on biomolecular interactions from a plurality of providers and processing such data to create and maintain images and/or text defining biomolecular interactions, said computer system, in response to data requests, creating and transmitting to a plurality of end-users, the images and/or text defining biomolecular interactions.

In an embodiment, a system for electronically managing, finding, and/or visualizing biomolecular interactions is provided comprising:

(a) a maintenance entity for receiving data on biomolecular interactions from a plurality of providers and means for receiving and processing such data to create and maintain images and/or text defining biomolecular interactions; and (b) one or more computer systems maintained by the maintenance entity and having means for creating and transmitting to a plurality of end-users the images and/or text defining biomolecular interactions.

The system is useful in managing, finding, and/or displaying biomolecular interactions including interactions involving proteins, nucleic acids (RNA, DNA), and ligands, molecular complexes, and signaling pathways. The interactions are defined both at the molecular and atomic levels and in particular they may be defined by chemical graphs.

The invention also provides a method for displaying on a computer screen information concerning biomolecular interactions comprising retrieving an image and/or text defining a biomolecular interaction from a system of the invention.

The present invention also provides a data structure stored in the memory of a computer the data structure having a plurality of records and each record containing a biomolecular interaction and information relating to the biomolecular interaction. In an embodiment the biomolecular interaction is identified by chemical graphs. The information in the data structure may be accessible by using indices which may represent selections of information from the chemical graphs.

The term "record" used herein generally refers to a row in a database table. Each record contains one or more fields or attributes. A given record may be uniquely specified by one or a combination of fields or attributes known as the record's primary key. A record of a biomolecular interaction as used herein is generally a record containing information identifying the biomolecular interaction as a chemical graph and a plurality of other attributes with information pertaining to the biomolecular interaction (e.g. information on the cellular place of interaction, experimental conditions used to observe the interaction, conserved sequence comment of molecules in the interaction if they are biological sequences, information on molecules in the interaction, description of metabolic and signaling pathways, cell cycle stages in which an interaction is involved, locations of binding sites on the molecules in an interaction, chemical actions mediated by the interactions, and chemical states of the molecules in the interaction).

The term "chemical graph" refers to a connectivity graph of all the atoms and bonds in a molecule in a biomolecular interaction. The graph may include three-dimensional coordinates.

The invention also provides a method for storing a representation of a biomolecular interaction in a memory of a computer system, the method executed on a computer system and comprising the steps of:

(a) identifying a chemical graph of a biomolecular interaction; and (b) storing a record in a data structure of the invention.

The invention further provides a method for storing a representation of a biomolecular interaction in a memory of a computer system, the method executed on a computer system and comprising the steps of:

(a) identifying a chemical graph of a biomolecular interaction;

(b) generating one or more indices from information in the chemical graph; and (c) storing a record in a data structure of the invention.

The invention still further provides a method for identifying a biomolecular interaction that is similar to a reference biomolecular interaction, the method executed on a computer and comprising the steps of:

(a) conducting a similarity search for each molecule in a test biomolecular interaction;

(b) screening the results of the similarity search preferably by selected taxonomy;

(c) assembling a putative biomolecular interaction to create a test record;

(d) accessing one or more records in a data structure stored in the memory, the data structure having a plurality of records, each of the records containing a reference biomolecular interaction and information relating to the reference biomolecular interaction; and (e) matching the test record with each record in the data structure to produce a matching record containing a reference biomolecular interaction matching the test biomolecular interaction.

The similarity searches may be based for example on sequence similarity or identity, or similarities in molecular weights, pIs, mass fingerprinting data or mass spectrometric data, fragment-ion tag data, peptide masses from enzymatic digestion, fragment ion masses, isotope patterns, and sequence tag data. Standard tools available in the art for similarity searching and screening can be used. (For example, the following tools may be used BLAST BioScan, Fasta3, PropSearch, SAMBA, SAWTED, Scanps, FDF, ExPASY Proteomics Tools TagIdent: PeptIdent:ProteinProspector:MultiIdent: PeptideSearch:PROWL:Mascot:BioSCAN, Pro).

Another aspect of the invention provides a computer system for storing a representation of one or more biomolecular interactions in a memory in the computer system and for comparing one or more reference biomolecular interactions to a test biomolecular interaction, comprising:

(a) a database means stored in the memory representing one or more biomolecular interactions; each of the biomolecular interactions represented by a chemical graph; and (b) a data structure means for storing a plurality of record means, each record means containing chemical graphs of the test biomolecular interaction.

The invention also provides a computer system comprising memory means, storage means, program means, and stored means for building virtual-models of biomolecular interactions in the computer system comprising:

(a) one or more libraries of reference biomolecular interactions that comprise any number of attributes or components of the biomolecular interaction which values are either being used to describe characteristics of the types of biomolecular interactions in the computer system, or values or data structures used by the program at runtime, or are to be used to more specifically describe characteristics of individual components of the biomolecular interaction that each instance of a type of biomolecular interaction is to represent, or characteristics of each instance of biomolecular interaction in the computer system; wherein the attributes have values of any type in the computer system or in a network accessible by the computer system;

(b) means for manipulating the biomolecular interaction by domain experts or program means comprising visual means for making the biomolecular interactions available through menus or palettes or programmatic means; and (c) constructor means to create new instances from the definitions of the biomolecular interactions, and means to establish directional output-input links between complemenatary instances of the biomolecular interactions directly or through components.

Also provided is a computer system comprising:

(a) a database having a plurality of records, wherein each record contains a reference biomolecular interaction defined by a chemical graph and descriptive information from an external database which information correlates the biomolecular interactions to records in the external database; and (b) a user interface allowing a user to selectively view information regarding a biomolecular interaction.

In an embodiment, a computer system is provided comprising:

(a) a database having a plurality of records, each of said records containing a reference biomolecular interaction defined by a chemical graph and descriptive information from an external database, which information correlates the biomolecular interactions to records in the external database;

(b) a processor in communication with said database and responsive to user input to access records in said database; and (c) a user interface allowing a user to provide user input to said processor to selectively view information regarding a biomolecular interaction.

Still further the invention provides a database system comprising a plurality of internal records, the database comprising a plurality of records, wherein each record contains a biomolecular interaction defined by chemical graphs and descriptive information from an external database which information correlates the biomolecular interactions to records in the external database.

In an embodiment the external database is PubMed. The interface of the computer system may further comprise user selectable links to enable a user to access additional information for a biomolecular interaction. The links may comprise HTML links. Additionally provided is a method of using a computer system to present information, or a method of presenting information pertaining to records of biomolecular interactions in a database, the records containing information identifying the biomolecular interaction and defining the biomolecular interaction by chemical graphs, the method comprising:

(a) providing an interface for entering query information relating to a biomolecular interaction;

(b) locating data corresponding to the entered query information; and (c) displaying the data corresponding to the entered query information.

In step (b) the data is located by examining records in the database.

The invention further provides a computer program product comprising a computer-usable medium having computer-readable program code embodied thereon relating to a plurality of records of biomolecular interactions, the records identifying the biomolecular interactions and defining chemical graphs of the biomolecular interactions, the computer program product comprising computer-readable program code for effecting the following steps within a computing system:

(a) providing an interface for entering query information relating to a biomolecular interaction;

(b) locating data corresponding to the entered query information; and (c) displaying the data corresponding to the entered query information.

The invention contemplates a database storing data relating to biomolecular interactions comprising:

(a) first data types describing biomolecular interactions between chemical objects;

(b) second data types describing collections of biomolecular interactions; and (c) third data types describing pathways between said collections of interactions.

The first data types may include objects for the chemical objects, each of the objects including at least one of a pointer to an external database describing the chemical object, a sequence, and a chemical graph. The first data types may be stored as records and further include objects identifying the biomolecular interactions and defining chemical graphs of the biomolecular interactions.

The second data types may include lists of identifications referencing the biomolecular interactions in the collections. The third data types may include objects for the chemical objects that can form networks of interactions. The networks of interactions may include metabolic pathways and cell signaling pathways. The third data types may additionally include sequences of identifications referencing biomolecular interactions that make up the pathways.

The systems and products of the present invention may be used to study and identify biomolecular interactions. Such information is of significant interest in pharmaceutical research, particularly to identify potential drugs and targets for drug development. The systems and products provide great power and flexibility in analyzing biomolecular interactions.

Further features and advantages of the present invention, as well as the structure and operation of various embodiments of the present invention, are described in detail below with reference to the accompany drawings.

DESCRIPTION OF THE DRAWINGS

The invention will be better understood with reference to the drawings in which.

DESCRIPTION OF PREFERRED EMBODIMENTS OF THE INVENTION

Figure 12:
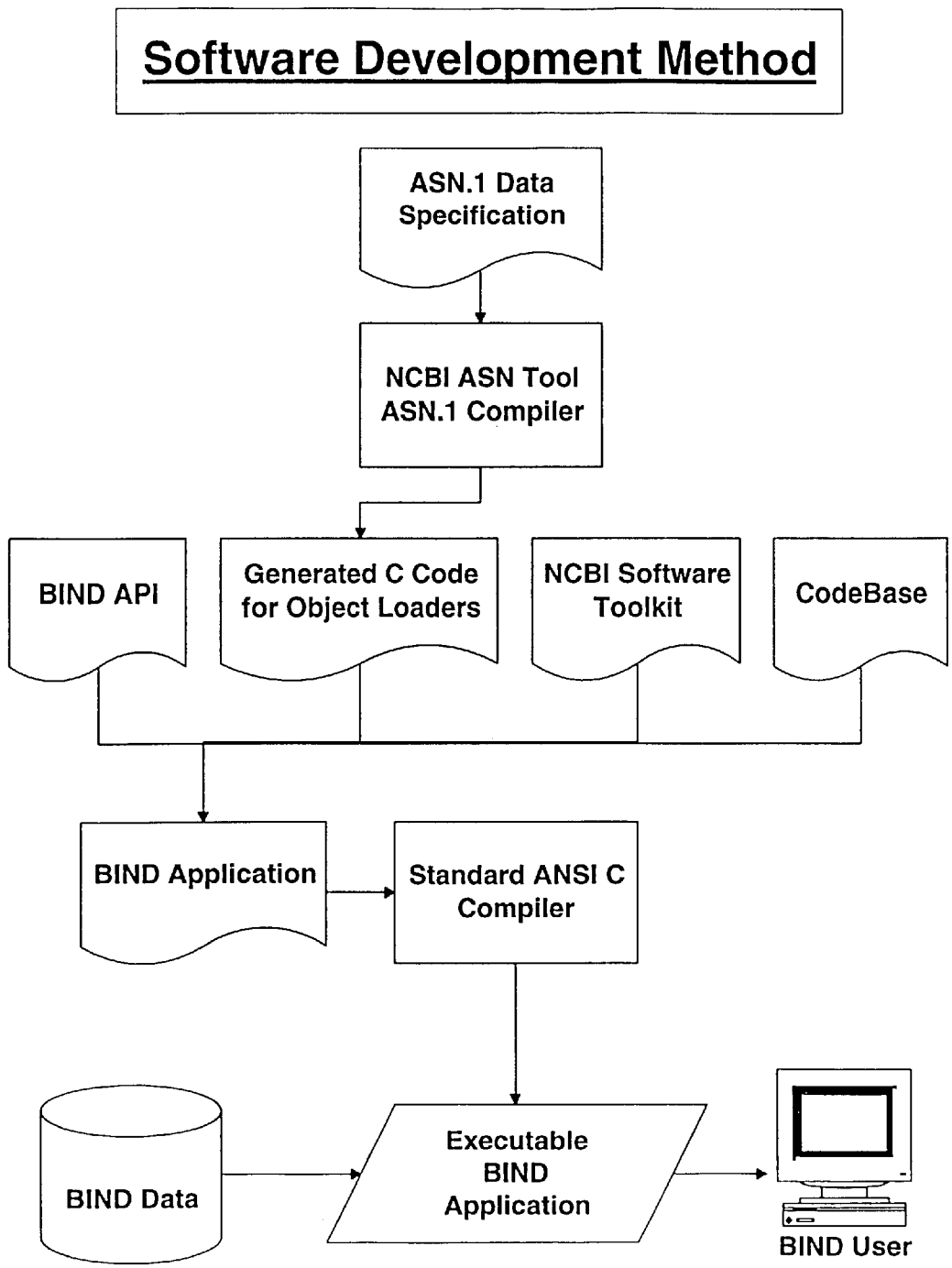
FIG. 12 is a schematic diagram showing a software development method.
Figure 13:
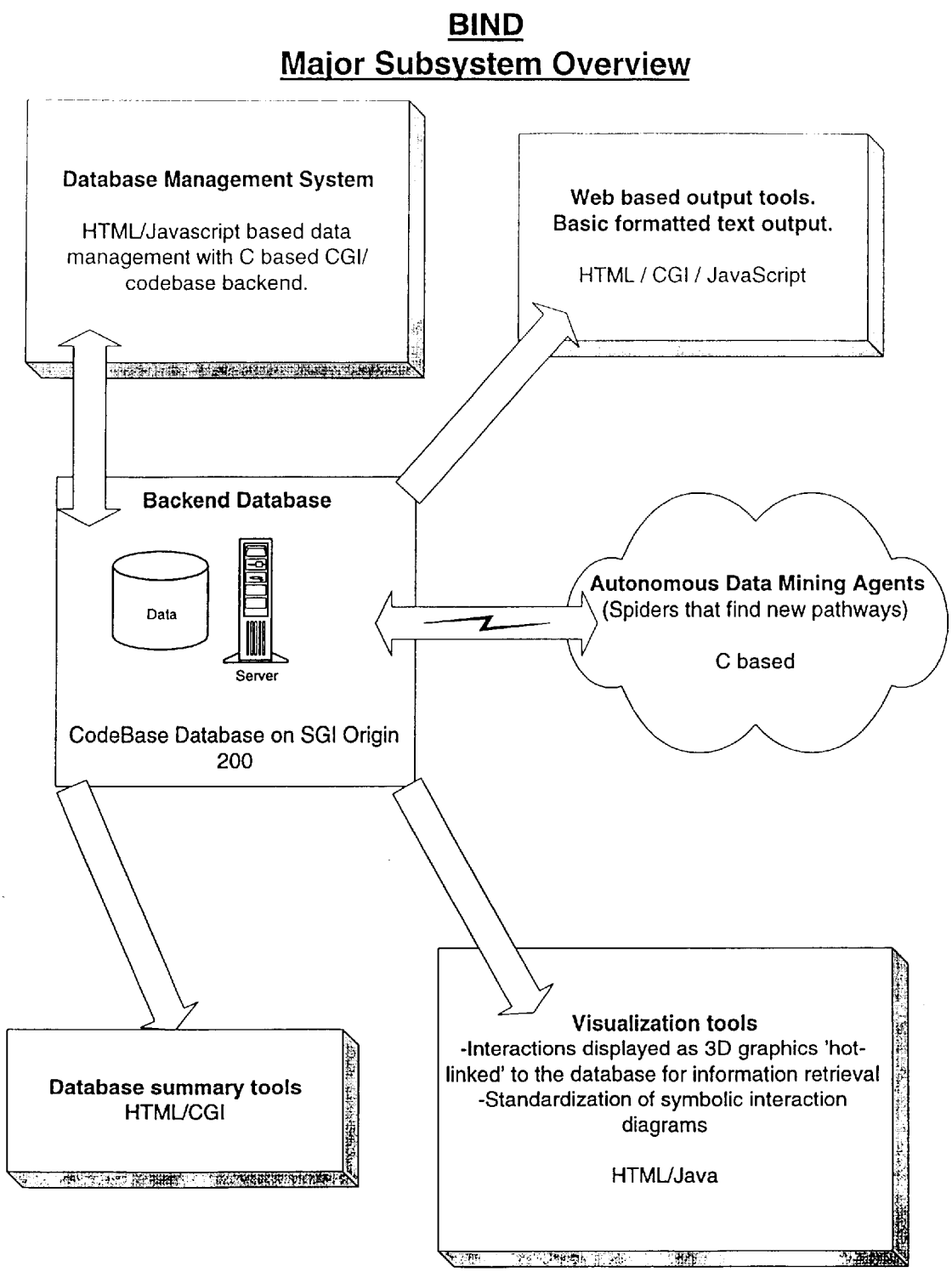
FIG. 13 is a schematic diagram showing a major subsystem overview of BIND.
Figure 14:
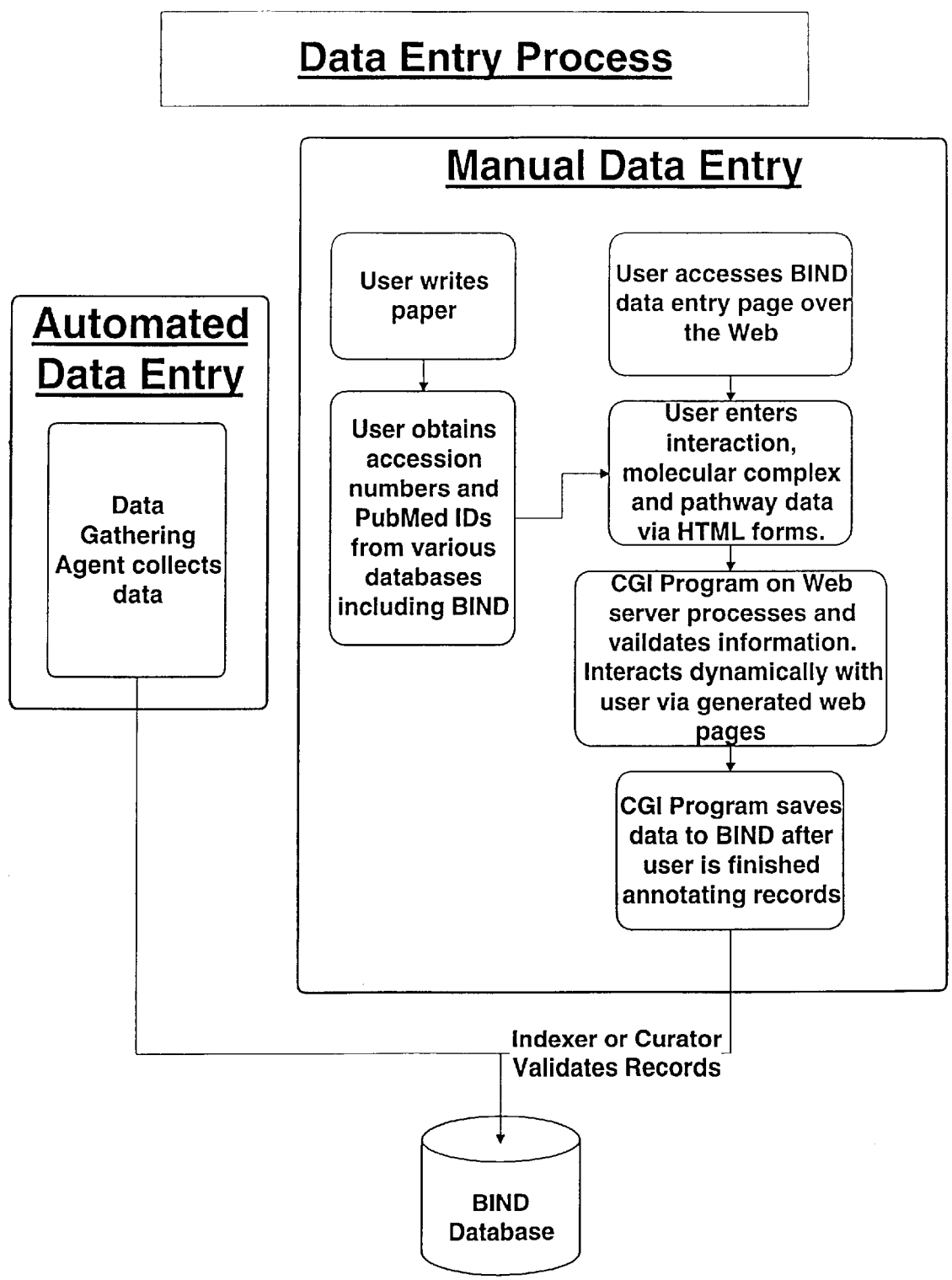
FIG. 14 is a schematic diagram showing the data entry process for BIND.

The present inventors have developed BIND or the Biomolecular Interaction Networks Database and its related tools for both the management and mining of molecular interaction data. BIND permits the rapid identification and visualization of new and known cellular pathways using bioinformatics methods, and it provides an understanding of these interaction pathways. BIND is stored in memory within a host computer system including one more computers that is responsible for maintaining BIND. Biomolecular interactions are received from internal and external providers through connections to the host computer network and are processed to maintain images and/or text defining the biomolecular interactions. Images and/or text defining biomolecular interactions in BIND can be conveyed to end-users through computer connections to the host computer system allowing end-users to display the biomolecular interaction data on the monitor display screens of their computers. (See FIG. 12 for a schematic diagram of the BIND software development method; FIG. 13 for a schematic diagram showing the major components of the BIND system; and FIG. 14 for a schematic diagram of a data entry process for BIND). In this way, biomolecular interactions can be electronically managed, located and/or visualized. Further details concerning BIND will now be described.

Biomolecular information is stored in records within BIND. A BIND record can describe any molecular interaction, stored in a BIND-object as a) a pointer to another database, b) a sequence or c) a chemical graph. Two BIND-objects that interact are held in an interaction record within BIND. The interaction record can represent the binding interaction at various levels of detail. BIND also stores kinetic information, bibliographic information, interaction locations, conserved sequences, mediating interactions, chemical reactions that take place and activation states of BIND-objects. BIND draws upon NCBI data format standards, and thus BIND is compatible with other public sequence and structure databases. BIND forms a data-space that can contain large molecular interactions, such as a protein signaling complex, to detailed descriptions of atomic level interactions. The design and database samples and tools to aid in web-based data entry and retrieval are described herein. A graphical system of data retrieval and data mining agents that scour this data space for novel links between known interaction pathways can be implemented based on this design.

The BIND Data Model

The three main types of data objects in the BIND specification—interaction, molecular complex and pathway—as well as useful database management and data exchange objects are described below. Each of the main objects is composed of various descriptor objects that are either defined in the specification or taken from the NCBI ASN.1 Data specification. For example, an interaction record contains, among other data object, two BIND-objects. These BIND-objects are themselves defined using simpler sub objects. Normally, a BIND-object that is describing a protein sequence will store a simple link to a sequence database, such as GenBank. If, however, the sequence is not present in the public database, it can be fully represented using an NCBI-Bioseq object. The NCBI-Bioseq object is how NCBI stores all of the sequences in GenBank and is a mature data structure.

BIND also inherits the NCBI/EMBL/DDBJ taxonomy model and data, and is designed so that interactions can be both inter and intra organismal. Below is an example of the types of biological data for each BIND record. Explanations of the various objects in the specification are given along with examples. The BIND specification is explained as if it were being used to describe a single record in a database.

The BIND database is generally meant to reference information from other databases rather than storing the information as a copy. This avoids unnecessary duplication of information among databases and helps maintain data integrity (if the information in a referenced record in one database is updated, the other databases that reference the record are all automatically updated). All fields are non-optional unless stated otherwise.

A BIND-object

Figure 1:
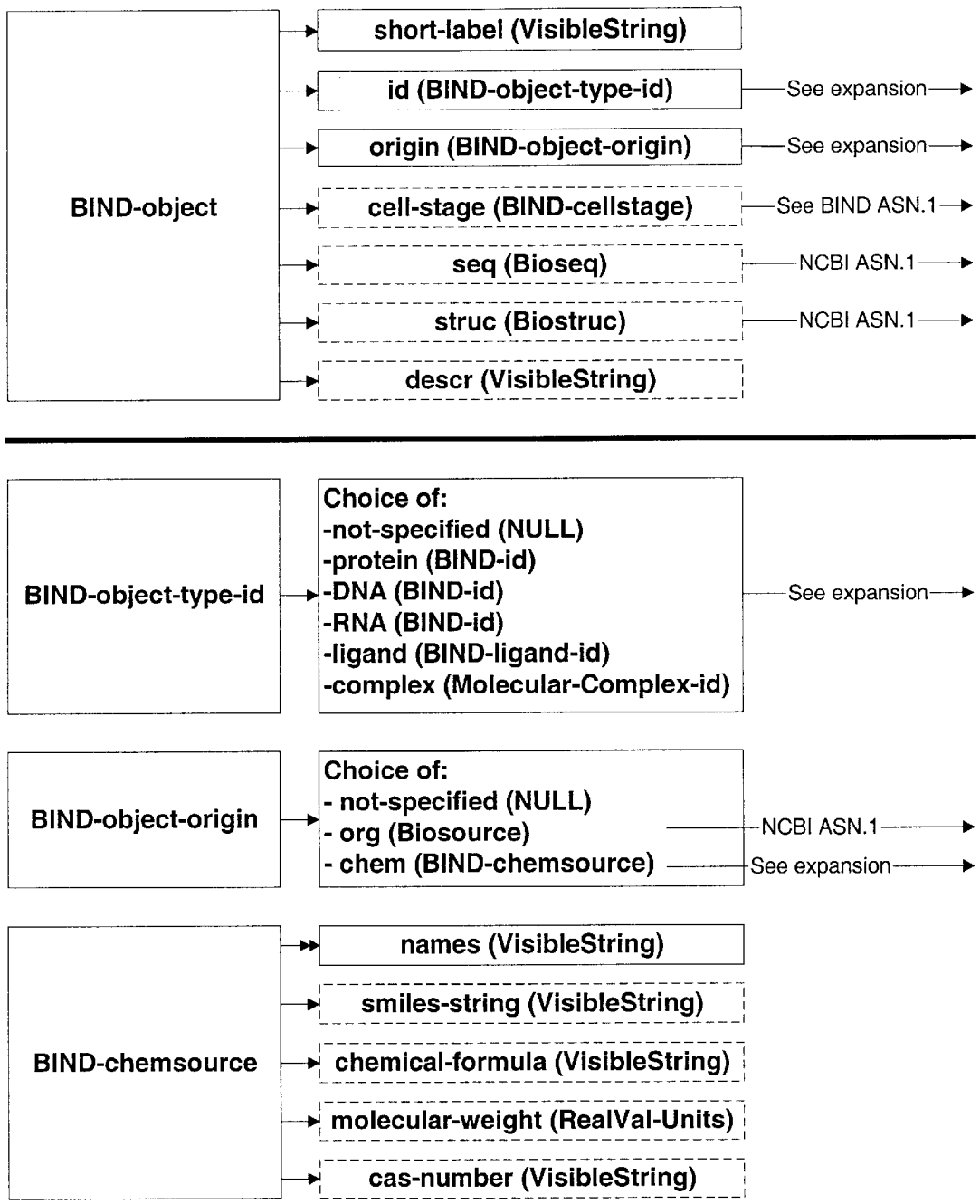
FIG. 1—Storing a chemical object—A BIND-object data type. A chemical object can be any molecule or atom. Associated data types are also shown. Legend: Each box is a data type. Dashed outline boxes represent ASN.1 fields marked as OPTIONAL. Single headed arrows point to expanded definition for a data type. Double headed arrows represent one to many relationships (repeated fields or objects).
Figure 2:
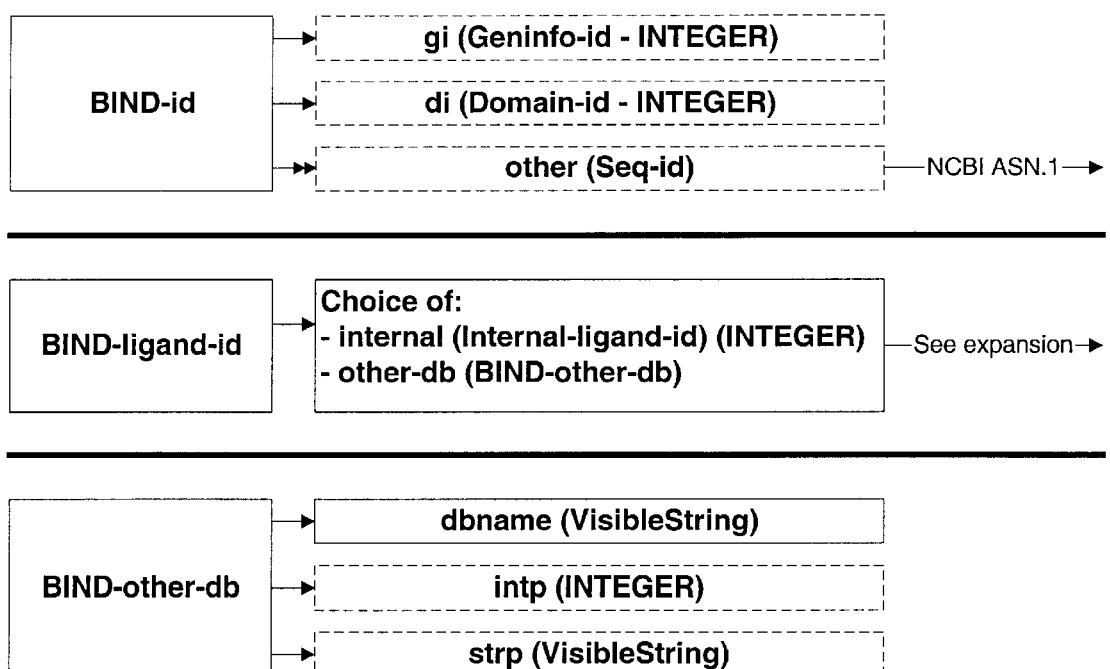
FIG. 2—Storing a chemical object (continued).

A BIND-object represents any chemical object—atom, molecule or complex of molecules. See FIGS. 1 and 2 for a diagrammatic description of the data type. A BIND-object contains:

1. A short-label field to contain a short name for a molecule. For example, ATP, IP3, S4 and HSP70 are acceptable short labels for ligands and proteins, respectively. Having a non-optional short label ensures that at least some descriptive data is entered for a molecule. This information is also useful to construct top-level descriptions regarding a particular record. For example, a simple description of an interaction between two proteins can be constructed using the short labels of the two BIND-objects in an interaction record. A graphical view of an interaction would be labeled with the short label field.

2. A BIND-object-type-id object to contain the type of the molecule and a reference to another database containing a record for that molecule. In this way, for instance, large DNA records are referenced rather than duplicated. A molecule type may be 'not-specified', 'protein', 'dna', 'ma', 'ligand', or 'molecular complex'. Molecules of unknown type may be stored by specifying the type of molecule as 'not-specified'. This type requires no further data input.

Protein, DNA and RNA all require a BIND-id object. This object can store accession numbers to any other database. It has special fields 'gi' or Geninfo and 'di' or domain identifier for the NCBI Entrez system (Schuler et al., 1996) and a database of domains, respectively. Any other accession number or numbers/strings to reference records in other databases can be stored in a set of NCBI Seq-id's present in the data object. All fields in BIND-id are optional so molecules stored internally in a BIND record that are not present in other databases (and so do not have accession numbers) can be properly saved.

Molecules of type 'ligand' require a BIND-ligand-id object. This object can contain a reference to an internal small molecule database or any other small molecule database via a database name and an integer and/or character based accession number.

BIND-objects of type 'complex' require an integer accession number to a BIND molecular complex record.

3. A BIND-object-origin data structure. This data structure contains a choice of origin between 'not-specified', 'org' or organismal, and 'chem' or chemical. BIND-objects of unknown origin would have origin type 'not-specified'. Chemical objects that are derived directly from organisms, such as DNA, would be specified to be origin type 'org' and are required to be associated with an NCBI BioSource object. A BioSource object can contain much descriptive data about an organism and the biological source of a compound. It also contains a reference to a taxonomy database. This information can be entered automatically if a GI is known for a biological sequence molecule, since a BioSource is part of the NCBI Bioseq object which stores biological sequences in Entrez. If a GI is not given, a BioSource can be created.

Molecules derived purely from chemical means are of origin type 'chem' and require a BIND-chemsource object. The BIND-chemsource object contains a set of names for the chemical, usually a common name and any synonyms, a SMILES string (Weininger, 1988), the chemical formula, molecular weight (a RealVal-Units object), and a CAS registry number (http://www.cas.org). A SMILES string is a standard way of representing a molecule's structure using ASCII characters. Many chemistry computer applications are available to manipulate and use data of this type. Three-dimensional structure of a molecule can be predicted from a SMILES string to a high degree of accuracy using commercial chemistry applications such as Corina (Gasteiger, 1996) and others. A CAS number is a reference number to the information regarding a chemical compound in the Chemical Abstracts Service. This service contains data on at least 22,468,564 chemical compounds. Of all the fields in a BIND-chemsource object, only 'names' is non-optional. This means that for a BIND-object to be declared a ligand of chemical origin, one must only provide a pointer to a small molecule database and one name of the chemical.

4. An optional BIND-cellstage list to contain a list of cell cycle stages in which this object is found, or expressed, in the given organism. This information is only relevant for BIND-objects of organismal origin. A BIND-cellstage object is an enumeration of all of the basic cell stages in the cell cycle. It contains an optional text description field that can describe other cell stages that are not present in the enumeration.

5. An optional NCBI Bioseq object to store a biological sequence if a record for the sequence is not present in any public database. The Bioseq may also be used to store the experimental form, such as His tagged proteins or mutants, of the biological sequence if it is different from any public database record. This field is only relevant for biological sequences. Bioseqs can be prepared using Sequin (Kans et al., 1998) and can be exchanged with NCBI.

6. An optional NCBI Biostruc object to store a three dimensional atomic structure of any chemical object, from an atom to a complex of molecules, if the data is not present in any public database. The Biostruc specification allows a chemical graph to be stored without coordinates. This is most useful for storing small molecule structures or post-translationally modified forms of a biomolecule. Thus, chemical entities within a BIND object can be described in precise detail.

The presence of these powerful and mature data structures in this part of the specification demonstrates that BIND is not completely reliant on other databases. Most of the information present in any public sequence or 3D molecular structure database can be stored using the BIND specification if necessary.

7. An optional free flow text description of the BIND-object. This field contains, for example, a full name for a molecule such as Adenosine Triphosphate (ATP).

BIND-Interaction

Figure 3:
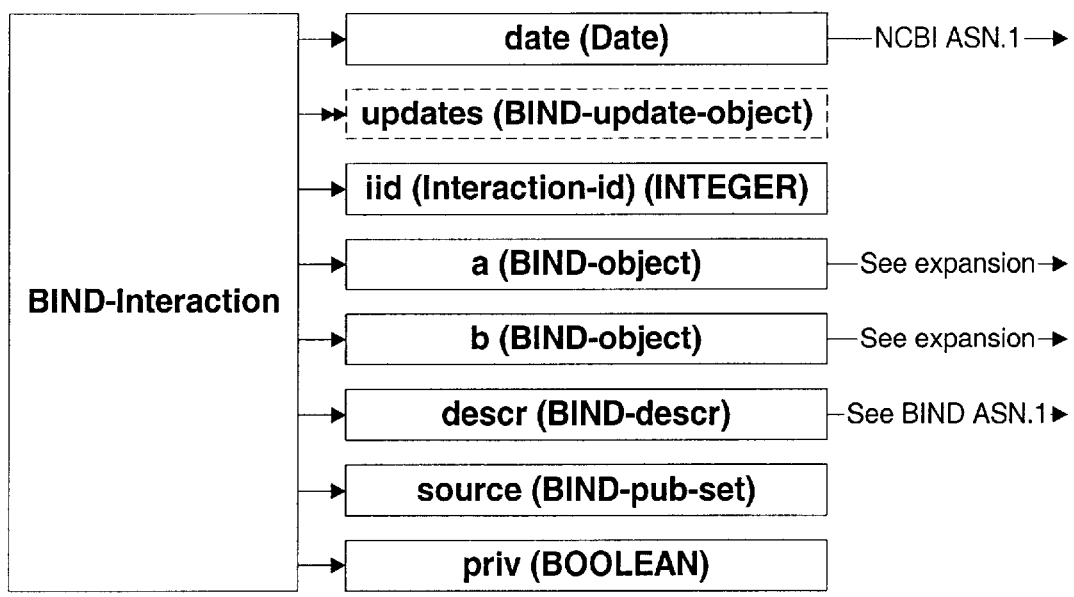
FIG. 3—Storing a biomolecular interaction—A BIND-Interaction data structure.

The BIND-Interaction object is the fundamental component for storing data in this specification. It defines and describes the interaction between any two molecules, or even atoms. The majority of the information that can be stored is, however, used to describe interactions between proteins, DNA and RNA. Interactions between molecules rather than between molecules and atoms are exemplified from this point on. See FIG. 3 for a diagrammatic representation of the data type.

A BIND-interaction contains a NCBI Date object, a sequence of updates for an audit trail, an Interaction Identifier (IID) accession number, two interacting molecules (BIND-object), a description of the interaction, a series of publications and a private flag. BIND IID number space is to be controlled using a unique key server. Molecule A binds to molecule B and both are stored using BIND-objects (described above).

The BIND-descr object stores most of the information in an interaction object. It contains text description of the interaction, information on cellular place of interaction, experimental conditions used to observe the interaction, conserved sequence comment of molecules A and/or B if they are biological sequences, location of binding sites on molecule A and B, chemical actions mediated by the interaction and chemical states of the molecules A and B.

A BIND-pub-set is included to store empirical evidence references, usually publications, that 'support', 'dispute' or have 'no opinion' regarding the actual interaction. The dispute flag allows the database to track experimental trends and offer a machine-readable way to find discrepancies or differences of opinion.

Finally, the private flag which defaults to FALSE is included in the BIND-interaction record. The flag indicates whether or not to export this record during a data exchange procedure. In a public database, a private record is not available to the public. This may be because the record has not been completed or information in the record has not been verified. In a private database, the private flag means that the record can be viewed internally, but not exported. In this situation, a private record might contain proprietary information. BIND may contain a mix of these and public records imported from a public database.

Interaction Description—BIND-descr

All of the objects directly linked in this structure are optional to allow any level of richness of data to be stored. BIND-descr contains:

1. A simple text description of the interaction. This free flow text is meant to be a short description of the interaction such as, "transcription factor X binds to a region of human DNA in section x of chromosome II".

Figure 4:
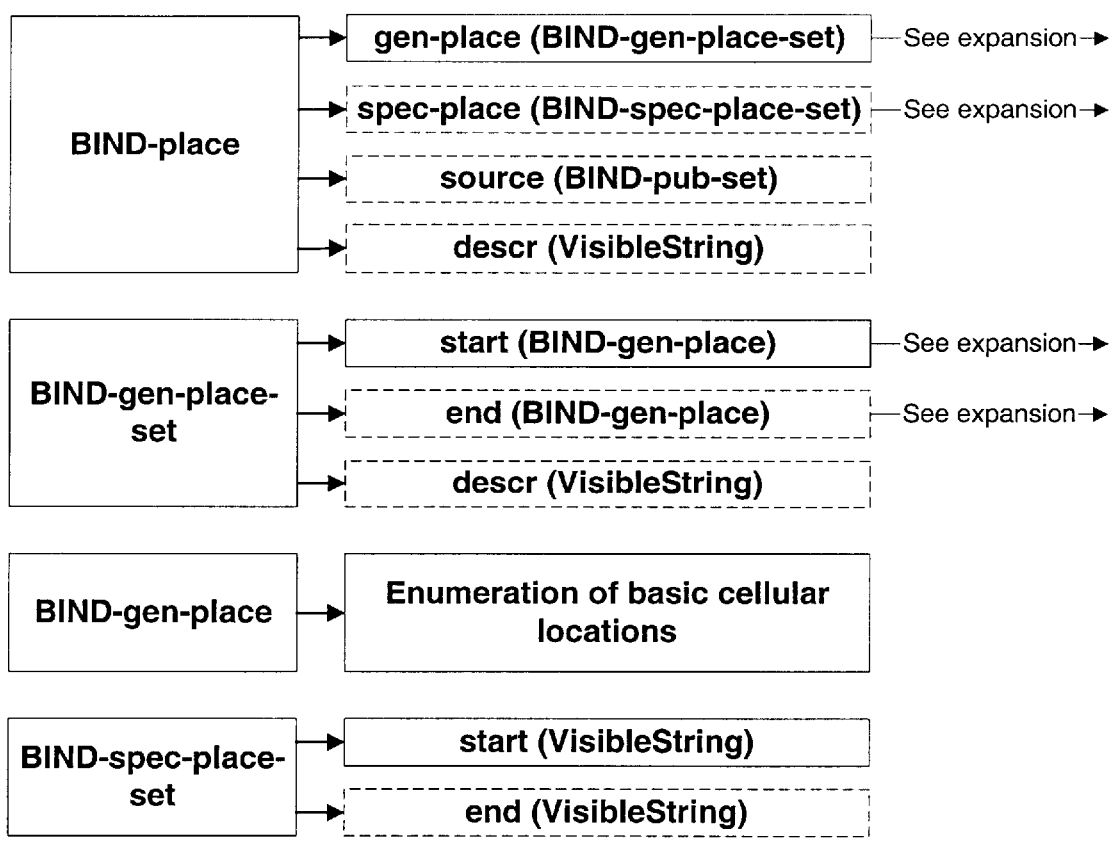
FIG. 4—Storing the cellular place information—A BIND-place object and associated data types. General place is saved using enumerated fields for computability and specific place is more detailed and human-readable.

2. A sequence of BIND-place objects. See FIG. 4 for a diagram of this data type. A BIND-place object stores information about the location of the interaction with respect to the cell. The place of an interaction is meant to be the location where molecule A and B come together in a biologically meaningful way. This object contains a BIND-gen-place-set object for storing general place data, an optional BIND-spec-place-set object for storing specific place data, an optional BIND-pub-set for storing publications referring to the localization of an interaction, and an optional text description field. A BIND-gen-place-set contains a start and an optional end place for the interactions, specified by an enumerated list of general places in the cell. Storing a start and an end place for an interaction takes into account the possibility of an interaction translocating across membranes and ending up in different subcellular compartments. The general enumeration of cell places allows a computer to understand the location of the interaction. Only basic cell places are present in the list. This is important for data visualization programs that need to be able to draw molecules in the correct places on a diagram of a cell. A human readable description of cellular place can be stored in the BIND-spec-place-set. This object contains a text description of a start and an optional end place for an interaction. More specific data regarding the location of interaction, such as in what part of a membrane, apical or basal, an interaction occurs can be stored in the BIND-spec-place-set object.

Multiple BIND-place objects are present to allow storage of an interaction that may be present only at certain separate places within and around the cell. More than one BIND-place object can also be used to describe an interaction occurring between two molecules over multiple sub-cellular compartments, as might be the case for transmembrane receptor proteins with large extra and intra-cellular domains.

Figure 5:
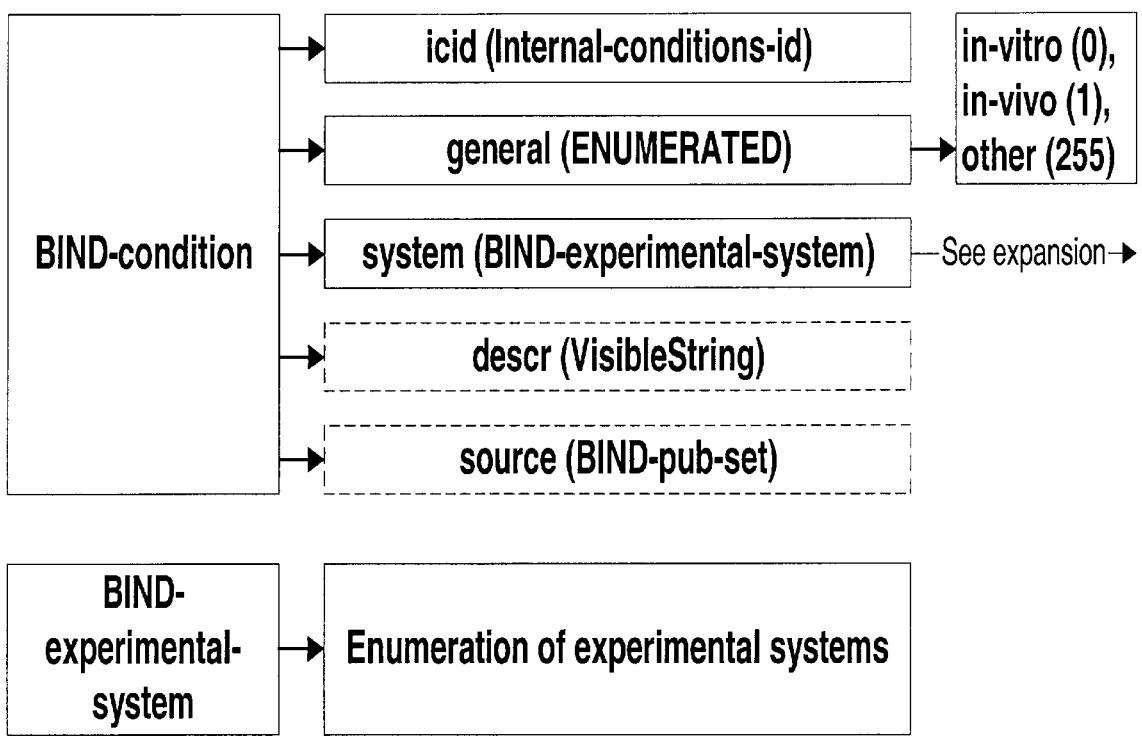
FIG. 5—Storing experimental condition information—A BIND-condition data object and associated data types.

3. A BIND-condition set to store a list of experimental conditions used to observe the interaction. See FIG. 5 for a diagrammatic view of the BIND-condition data type. Experimental conditions information stored should be sufficient to allow recreation of the original experiment. An experimental condition is described using a BIND-condition object. This object contains an Internal-conditions-id (ICID) number which can be used to reference a particular experimental condition in the BIND-condition-set. A general experimental condition is an enumeration of three general conditions, in-vitro, in-vivo and other. A BIND-experimental-system object is present and is an enumeration of most popular experimental techniques, with 34 techniques listed in the specification. This field has been simply declared as an INTEGER enumeration type so that it can be easily extended with new experimental systems as they become available. Declaring a type as INTEGER in ASN.1 instead of enumeration prevents generated code from checking the name of the enumerated value against the specification. This means that items may be added to the list at a later date without disrupting tools that are based on previous specifications. A BIND-condition object also contains a free human readable text description. This field could be used to describe a system further or could be used to name a system if 'other' has been specified as the BIND-experimental-system object. A BIND-pub-set is also provided in order to store publications related to the experimental systems described in the BIND-condition object.

Figure 6:
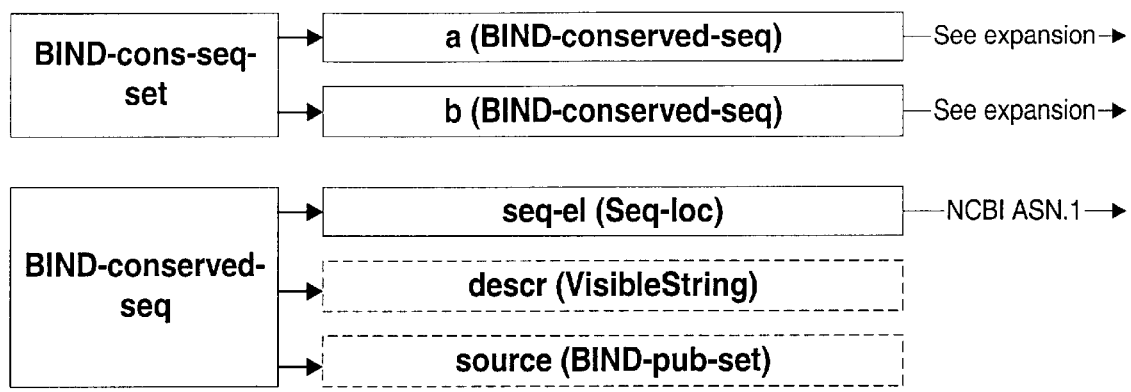
FIG. 6—Storing conserved sequence information—a BIND-conserved-seq object and associated data types. Conserved sequence may be stored for molecule 'a' or 'b'.

4. A BIND-cons-seq-set to store information about evolutionarily conserved sequence if either molecule A or B is a biological sequence. See FIG. 6 for the diagram of this data object. This information is simply meant to be a comment on the possible importance of certain sequence elements that have been noticed to be conserved via phylogenetic or other evolutionary analysis. It is possible that information about conserved sequence is known for molecules in an interaction that is not very well characterized. This data might be useful to investigators interested in further studying the interaction. A BIND-cons-seq-set contains conserved sequence information about molecule A and B in a BIND-conserved-seq object. Semantically, a BIND-conserved-seq object may only be instantiated with data if the molecule that it refers to is a biological sequence. A BIND-conserved-seq object contains an NCBI Seq-loc object. A Seq-loc can contain a location or a set of locations for any linearly numbered biological sequence. A free text description is also included in a BIND-conserved-seq. It is suggested that the method of determining the conserved sequence, for example a phylogenetic tree program such as PHYLIP or an alignment program such as PSI-BLAST (Altschul et al., 1997) or CLUSTAL (Higgins et al., 1996) be stored in the 'descr' field. A BIND-pub-set object is provided to store publications pertaining to a conserved sequence comment.

Figure 7:
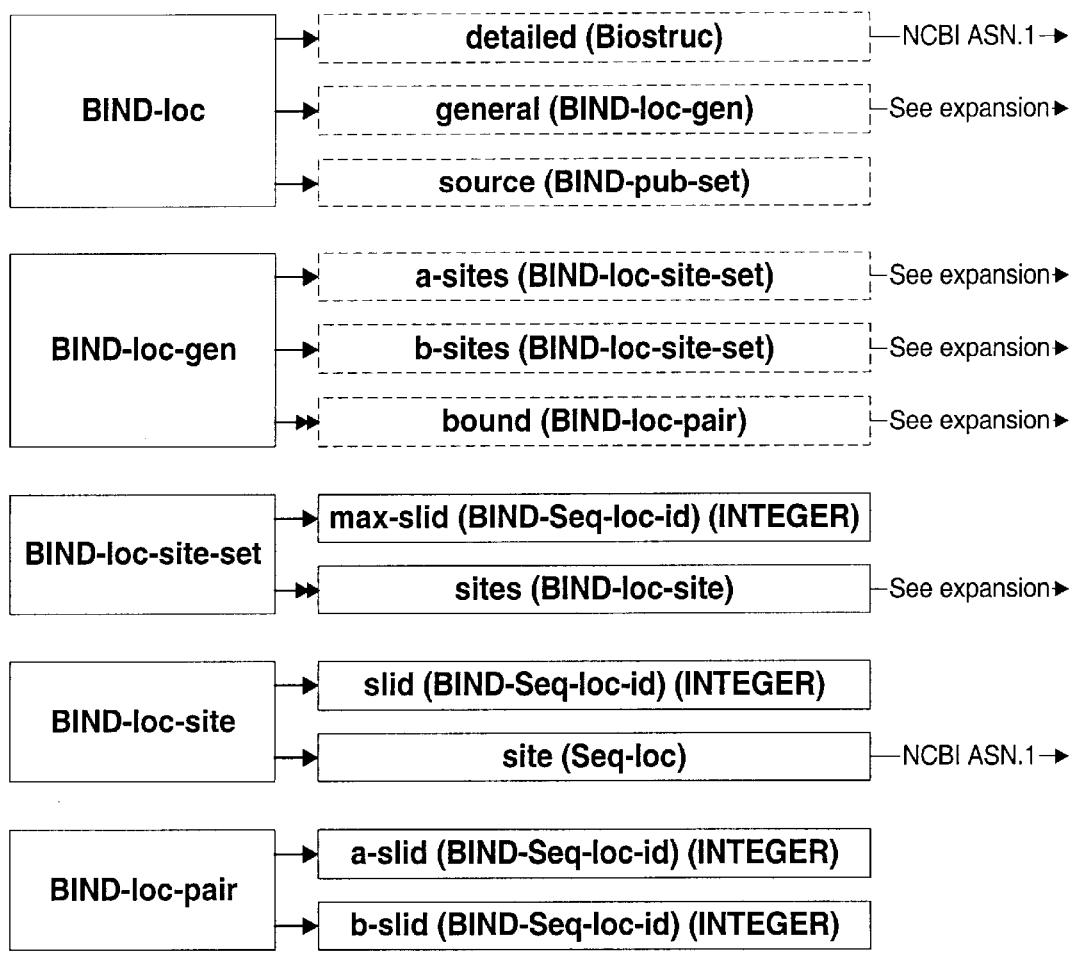
FIG. 7—Storing binding site location—A BIND-loc object and associated data types. Any number of binding sites may be stored for either molecule 'a' or 'b' in an interaction.

5. A BIND-loc to store binding site information. FIG. 7 contains a diagrammatic view of this data type. The BIND-loc can store 3D atomic level detail of an interaction site using an NCBI Biostruc. A BIND-loc-gen object is present to store binding sites in an interaction at the sequence element level of detail. Therefore, only interactions involving biological sequences can hold general binding site information. The BIND-loc object also includes a BIND-pub-set for storing publications related to binding site. All top level fields are optional allowing detailed, general and/or source information to be represented. Expanding further, the BIND-loc-gen object contains a list of binding sites on molecule A and a list of binding sites on molecule B. This information is contained in a BIND-loc-site-set object which contains a sequence of binding sites defined in BIND-loc-site objects. Each BIND-loc-site element contains an NCBI Seq-loc element and an internal reference integer ID called a BIND-Seq-loc-id. Since each binding site is numbered in a BIND-loc-site-set, it can be referenced by other objects.

A BIND-loc-gen object also contains an optional BIND-loc-pair object which specifies which binding sites on A bind to which binding sites on B. The binding sites are referenced from the BIND-loc-site-set objects so in order to use a BIND-loc-pair object, binding sites on molecule A and B must already be defined. This simple binary mapping allows most experimental binding information, such as that generated from footprinting analysis, to be stored.

Figure 8:
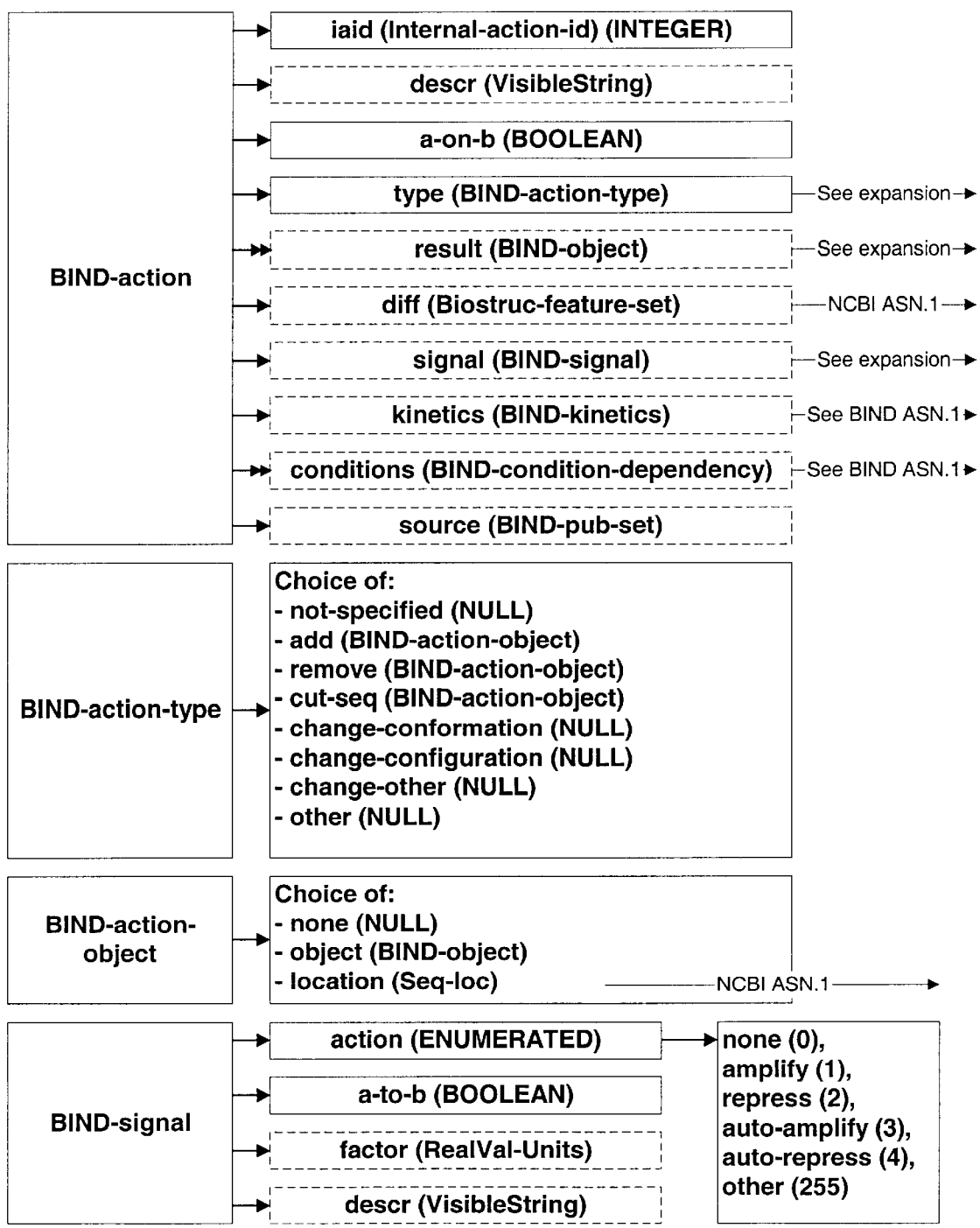
FIG. 8—Storing chemical actions—A BIND-action object and associated components. Any number of chemical actions may be stored in an interaction.

6. A set of BIND-actions to describe the chemical action (s) mediated by this interaction. FIG. 8 shows a diagram of this data type and related objects. A set of actions is required because there are many examples of interactions having multiple chemical actions. For instance, a kinase may phosphorylate a protein more than once in separate chemical actions or a restriction enzyme may cleave a molecule of DNA in more than one place. A BIND-action-set contains a set of elaborate BIND-action objects. Each BIND-action object in a set is numbered with an Internal-action-id (IAID) integer so that it can be referenced by other data types.

A BIND-action object contains an IAID number, an optional text description field for free flow text description of the chemical action and an optional BIND-pub-set for storing publications pertaining to this chemical action. A boolean flag is included to specify the direction of the chemical action. If a-on-b is set to true, then molecule A acts on molecule B, and vice versa. This value defaults to true. The type of action is defined in the BIND-action-type object. The BIND-action-type object is a choice element that stores the type of chemical action and an associated data object. The possible choices of actions are 'not-specified' for an unknown chemical action type, 'add' for adding a chemical object, 'remove' for removing a chemical object, 'cut-seq' for a cut in a biological sequence, 'change-conformation' for a change in conformation, 'change-configuration' for a change in configuration, e.g. by an epimerase or isomerase, 'change-other' for another type of change, such as a metal ion exchange, and 'other' for any other chemical action. Types 'add', 'remove' and 'cut-seq' are associated with a BIND-action-object to store related data.

A BIND-action-object is a choice element that can store nothing, with a choice of NULL, a BIND-object, or a site on a sequence using a Seq-loc. The 'object' choice of the BIND-action-object is only relevant for the 'add' and 'remove' choices of the BIND-action-type. The BIND-object is meant to store a description of the chemical compound that is added or removed. An example would be a phosphate group that could be added by a kinase enzyme or removed by a phosphorylase enzyme. The 'location' choice of the BIND-action-object is only relevant for the 'cut-seq' choice of the BIND-action-type. The Seq-loc is meant to store the position(s) where a biological sequence is cut. An example would be the locations after which a restriction enzyme cuts DNA or the sites after which a protease cleaves in a protein. The choice of 'none' can be used for either 'add', 'remove' or 'cut-seq' if information that would otherwise be stored is not known.

The BIND-action object also includes an optional result field to store the resulting molecule(s) from a chemical action as a sequence of BIND-objects. For instance, if a molecule of DNA was methylated, the description of the methylated DNA could be stored in a BIND-object. If a protein molecule was cut at various locations, all resulting protein molecule fragments could be described with the BIND-object sequence. With a sequence of interacting proteins where A binds to B, B binds to C, etc., the result field storing the full chemical form of B in the A—B interaction, for example, could be used directly in the B—C interaction record. This allows the exact description of sequential chemical modifications on a biological sequence that would otherwise not be possible given the standard sequence representation alone.

A Biostruc-feature-set that can contain residue or atomic level of detail differences in a molecule created by this chemical action is also present as a BIND-action object. The molecule that is different in this case is based on the direction of the chemical action. If the direction is molecule A to B, any information stored in the diff field would pertain to molecule B, not A. This field allows even small changes to molecules to be represented, as in the example of a chemical action reducing a double bond by adding two hydrogen atoms across it. The addition of the two hydrogen atoms could be recorded as differences on an atomic structure. This information requires the presence of atomic level detail data for the molecule being changed. The diff field can also represent changes made to the substrate of the chemical action. In an example of a phosphate added to a protein on a specific tyrosine residue by a phosphokinase enzyme, the diff field would simply be the position in the protein sequence of the tyrosine that was being changed.

An optional BIND-signal object is included in the BIND-action object to store directional information related to chemical signal as it is found in cell signaling pathways. This data is really a more general notion of kinetics describing signal transduction. The signal could, for example, be the activation of proteins in a signaling cascade via phosphorylation such as in a MAP kinase pathway. BIND-signal object contains an enumerated type describing the signal modification from a top-level viewpoint. Possible values are 'none', 'amplify', 'repress', 'auto-amplify', 'auto-repress', and 'other'. The direction of the signal is stored in the a-to-b boolean flag, which defaults to true. If a-to-b is true, the direction of signal is from molecule A to molecule B and vice versa. An optional RealVal-Units field can store the factor of signal amplification or repression if they occur. Signal amplification in the cell is really just the recruitment of molecules one step further down in the pathway by the molecule at the current step. So, if molecule A activates molecule B by removing a phosphate in a signaling pathway and there is amplification at this step, in the cell, molecule A activates many molecules of B causing a strengthening of the chemical signal by a measurable factor that may be stored. An optional free text description is available in the BIND-signal object as well. This field should contain some description of the signal action if 'other' is specified in the 'action' field.

Kinetic and thermodynamic data may also be optionally stored in the BIND-action object using the BIND-kinetics object. The BIND-kinetics object offers specified real value and text description fields for common kinetics (e.g. Michaelis-Menten) and thermodynamic values as well as providing a sequence of BIND-kinetics-other objects to store any other text or real number values that may be pertinent. A BIND-pub-set object is also present to store publications that relate to any of the information stored. All objects in the BIND-kinetics object are optional to allow any combination of values to be stored.

Also in the BIND-action object, a link to a sequence of experimental conditions used to observe this chemical action is optionally provided using a sequence of BIND-condition-dependency objects. The BIND-condition-dependency objects reference previously defined experimental conditions by Interaction-id and Internal-conditions-id number. In this way, any experimental condition in a database using this specification may be uniquely referenced.

Figure 9:
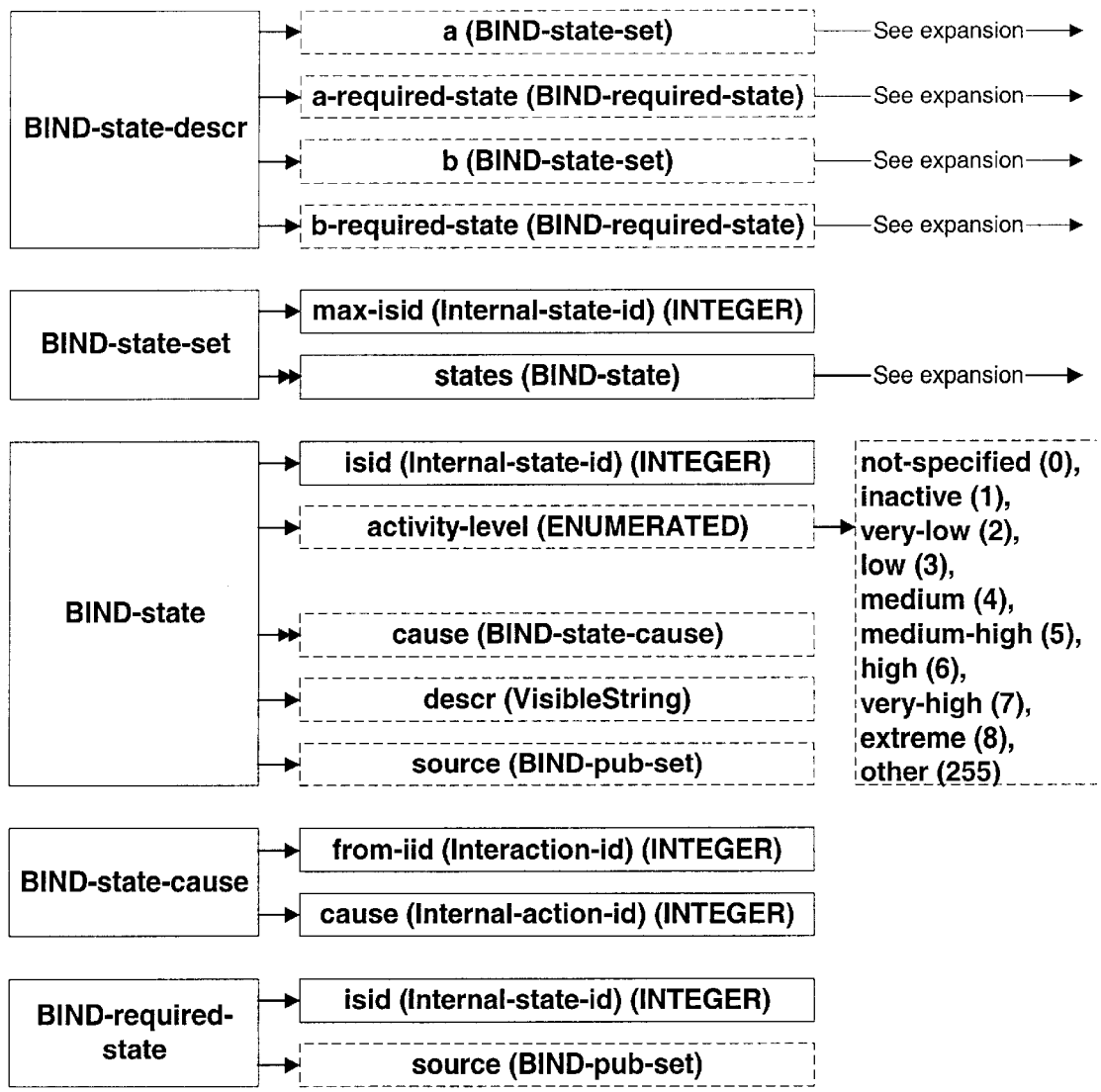
FIG. 9—Storing chemical state—A BIND-state data type and associated objects. Any number of chemical states may be stored in an interaction.

7. A BIND-state-descr object for storing information on chemical state of molecule A or B. See FIG. 9 for a diagrammatic view of this data type. The BIND-state-descr object stores a list of possible chemical states for molecules A and B in BIND-state-set objects as well as references to defined chemical states of A and B that are required for the interaction to take place, in BIND-required-state objects. More than one possible state can be saved because certain molecules can assume multiple states. One example is a protein enzyme which may be multiply phosphorylated to bring about different enzymatic activity levels, depending on the phosphorylation level. All fields in the BIND-state-descr object are optional allowing any combination of data objects to be stored. A BIND-state-set contains a sequence of BIND-state objects each numbered by an Internal-state-id (ISID) integer. Each BIND-state object contains an optional enumerated list describing the general activity of the molecule, an optional sequence of BIND-state-cause objects, an optional free text description, and an optional BIND-pub-set for storing publications related to this chemical state description. The 'activity-level' list is a simple description and is purely subjective, but is still useful for discriminating various states of different activity, especially by a data visualization program which could colour molecules based on this information.

The BIND-state-cause object can be used to uniquely reference previously defined chemical actions from this or other interactions that bring about this state. It contains an IID and an IAID. This functionality is very important in the specification because it allows full chemistry to be described when chemical actions and chemical states are taken together. Full chemistry means that all substrates, enzymes, products, bio-processed compounds etc. may be represented in full atomic level detail for all steps in a pathway. A certain chemical action can have a result (in the 'result' field of a BIND-action object) and a certain chemical state can reference the action that occurred to create it. In this way bi-directional linked lists can form networks that represent true chemical networks in a cell.

A Molecular Complex—BIND-Molecular-Complex

Figure 10:
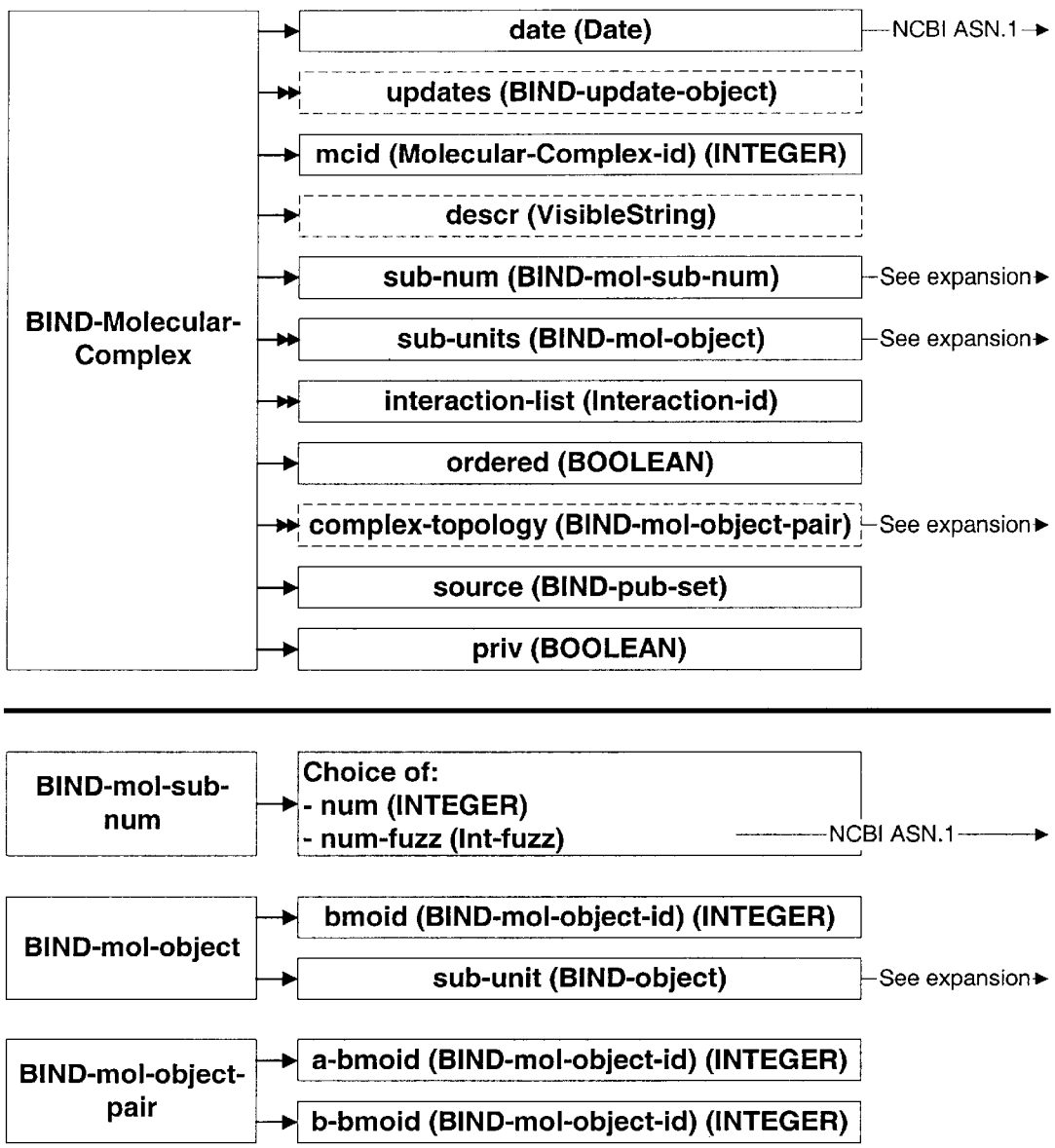
FIG. 10—Representing molecular complexes—A BIND-Molecular-Complex object and related data types.

The BIND-Molecular-Complex object is the second of three top-level biological objects in the BIND specification. It is meant to store a collection of more than two interactions that form a complex, i.e. three or more BIND-objects that can operate as a unit. In this way, it is useful to store knowledge of molecular complexes and as a shorthand for use when defining interactions and pathways (see BIND-pathway). FIG. 10 provides a box diagram view of this data type.

A BIND-Molecular-Complex object contains similar administrative information fields as a BIND-Interaction object. A Molecular-Complex-id (MCI)) integer accession number is stored to uniquely identify molecular complexes. A BIND-pub-set is present to store publications that concern this molecular complex and a private flag is provided to mark this record as private using the same rules as the private flag of the BIND-interaction record.

Six other fields in the molecular complex store data directly relating to the complex. A 'descr' field optionally provides space for a human readable free text description of the molecular complex. The 'sub-num' field contains a BIND-mol-sub-num object that stores the number of sub-units (BIND-objects) in the molecular complex. The sub-unit number includes either an exact integer using the 'num' field or a fuzzy integer in the 'num-fuzz' field. The fuzzy number is stored using an NCBI Int-fuzz object which can store a number in a range, plus or minus a fixed or percentage amount, or store a set of alternatives for the number. Using a fuzzy number, complexes can be stored even when the exact number of sub-units is not known. Examples of such complexes are actin filaments or other parts of the cytoskeleton and virus coat proteins, both of which typically form using repeated units of a certain protein.

The BIND-Molecular-Complex object also includes a 'sub-units' field to store the actual sub-units of the complex as a sequence of BIND-mol-object data types. The BIND-mol-object is simply a wrapper for a BIND-object that allows the BIND-object to be numbered using a BIND-mol-object-id integer (BMOID). Numbering the sub-unit BIND-objects allows the BIND-mol-object-pair to reference them for topology, as discussed below.

A primary component of the BIND-Molecular-Complex object is a list of Interaction-ids, which references previously defined interactions in a database. This means that most of the data for function, state, location, etc. for a molecular complex is actually stored in BIND-Interaction objects. This avoids some duplication of information. A boolean flag marks the interaction list as being ordered or not. This should be true if the temporal order of interactions that form the complex is known and the IID list is ordered in that way. Ordering of sub-unit binding for some well studied biological complexes, such as the ribosome, is known.

An optional sequence of BIND-mol-object-pair objects is present in the BIND-Molecular-Complex object and is meant to store a two-dimensional topology of the molecular complex. A BIND-mol-object-pair object simply records a connected pair of BIND-mol-objects in the molecular complex by making a reference to two BMOID numbers of the sub-units that are connected. Together the BIND-mol-objects, as nodes, and the BIND-mol-object-pair objects, as edges can describe the computer science concept of a graph. The topology information can allow a data visualization program to draw a representation of the actual shape of the complex.

Because most of the data for complexes is referenced BIND-interaction records, a certain amount of automatic data entry can be used. A list of sub-units and the number of sub-units can be automatically entered by fetching the data from the given list of interaction records.

It can also be noted that a molecular complex can be defined if the pairwise interactions of which it is composed are not completely known. This can be done by creating a set of interaction objects with molecule A as a sub-unit of the complex and molecule B as 'not-specified'. This is useful since many preliminary studies of a molecular complex observe only that certain molecules interact, e.g. from gel data, but not how they interact.

A Pathway—BIND-Pathway

Figure 11:
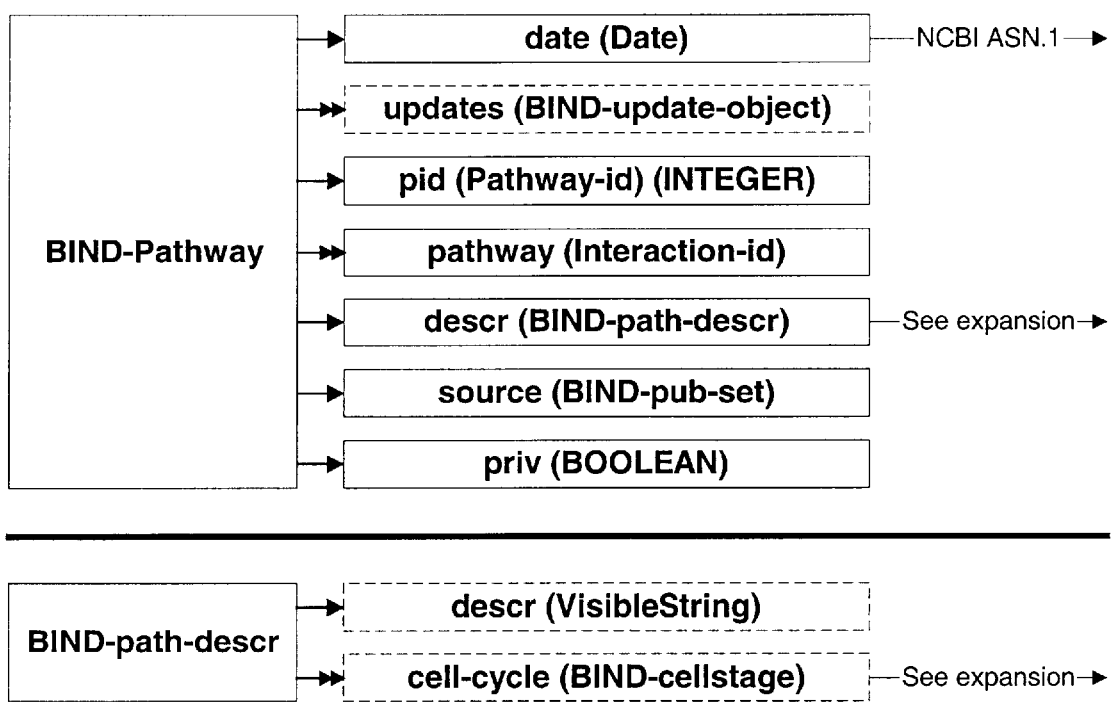
FIG. 11—Storing biochemical pathways—A BIND-Pathway object and associated data types. Cell cycle information can be stored.

The final top-level biological object in the BIND specification is the BIND-pathway data type. It describes a collection of more than two interactions that form a pathway, i.e. three or more BIND-objects that are generally free from each other, but can form a network of interactions. Common examples include metabolic pathways and cell signaling pathways. See FIG. 11 for the box diagram for this data type.

A BIND-Pathway object contains similar administrative information fields as a BIND-Interaction and a BIND-Molecular-Complex. Two other fields in the BIND-pathway object store information describing the pathway. A sequence of Interaction-ids that reference previously defined interactions that make up this pathway is stored. Extra descriptive information regarding the pathway is stored using a BIND-path-descr object. This object can optionally store free text describing the pathway and an optional sequence of BIND-cellstage objects that represent the phases of the cell cycle in which this pathway is in effect. Parts of the pathway may be constitutively present in the cell, while other parts that complete the pathway and allow activation may only be expressed at certain times during the cell cycle.

Other BIND ASN.1 Objects

Publication Set

A BIND-pub-set is used to hold all publications in BIND. It contains a list of BIND-pub-objects and a dispute flag. A BIND-pub-object contains an optional free text description of the publication, an enumerated opinion of the publication field and a NCBI Pub object. The description field may hold any text data pertaining to the publication referenced by this object. The opinion field may hold the values: 'none', 'support' and 'dispute'. It is meant to convey the general opinion of the referenced publication in regard to the information in the ASN.1 object that contains the BIND-pub-set. The NCBI Pub object is used to store most of the data in PubMed and can represent almost any publication. It should be used to store a reference to PubMed whenever possible using either a Medline Unique Identifier (MUID) or a PubMed unique identifier (PMID).

Record Update

If a record is updated in BIND, a description of the update should be added to a BIND-update-object. This object contains a NCBI Date object and a text description field. The description field may contain any information that a database implementation decides to store, but it should be complete and stored in a standard and automatic way within each implementation so that it can be easily parsed. Any information may be stored up to and including the entire previous record in ASN.1 value notation. This data is not meant to be human entered but rather maintained as a machine generated audit trail of any changes made.

Data Exchange and Data Cross-referencing

Data exchange systems and database management data structures have been included in the specification as powerful tools to make implementations more robust. BIND-Submit is the top-level object for data exchange while the cross referencing system involves many separate top-level data objects.

Data exchange—BIND-Submit

The BIND-Submit object can be used to exchange any number of the top-level data types in the BIND specification, BIND-Interaction, BIND-Molecular-Complex, and/or BIND-Pathway objects. BIND-Submit stores an NCBI Date object, an optional BIND-Database-Site, a BIND-Submitter object, an optional BIND-Submit-id integer for identifying this submission, and fields for optionally storing BIND-Interaction-set, BIND-Complex-set, and BIND-Pathway-set objects.

A BIND-Database-site is a description of a database site. This object could be used if data was being submitted to BIND from any other database. It contains free text description of the database site, usually the database name. Also present is a text field for database country of origin and an optional field used to store the World Wide Web Universal Resource Locator (WWW URL) of the homepage of the database on the Internet. An optional NCBI Pub object can store a Medline reference for this database.

A BIND-Submitter object contains information about a submitter to a BIND database. BIND-Submitter stores a BIND-Contact-info object which contains information about a person. A "hold until published" boolean flag is present which defaults to false to allow data submission prior to publication. Also present is an optional enumeration of possible submission types, either 'new', 'update', 'revision', or 'other'. An update is a change by an author while a revision is a non-author update. A free text field, 'tool', stores the name and version of the tool used to submit the record.

Personal contact information may be kept separate from BIND records to keep the submitter and ownership information anonymous and protected from improper use.

Actual records are stored in the BIND-Submit object in data set data types. The BIND-Interaction-set, BIND-Complex-set and BIND-Pathway-set are all present in the BIND-Submit object and are analogous in that they optionally store the date on which the set was collected, optionally the database from which the record set originates using a BIND-Database-site, and the respective sequence of records.

Cross-Referencing the Data

Since the BIND specification describes biological data from interactions to pathways and networks of pathways, the information space represented resembles a largely undirected graph with molecules as vertices and their interactions as edges. Cross-referencing information allows the graph to be easily traversed using simple indexed lookup techniques. If cross-referencing were not used in a system such as this, all records would have to be examined at each traversal of the data space. Instead of creating traditional large, unwieldy indexes and tables to speed the traversal process, ASN.1 objects are directly specified to store cross-reference information. This represents an object oriented database index system. Each BIND database accession number as well as NCBI GI, MUID and PMID and SLRI DI accession numbers has its own associated cross-reference object. This information may be easily exported and used by other databases to link their sequence or structure data back to BIND.

When updating cross-reference information, only one level of the graph is traversed, so as not to make the index overly complicated. Any time one of the three top level objects is created that contains a cross-referenced accession number, the BIND-Cross-Ref object lists are updated. In this way, any search using a cross-referenced accession number instantly retrieves all of the interaction, complex and pathway records that contain it.

The interaction cross-reference data is stored in a BIND-Iid-Cross-Ref object. This data type contains the IID of the interaction being cross-referenced in this object. The 'ids', 'pids' and 'mcids' fields contain a list of IIDs, PIDs and MCIDs, respectively of interactions, pathways and complexes that contain this interaction. A BIND-Submitter object is included to privately store submitter information for every interaction.

Molecular complex cross-reference information is stored in a BIND-Mcid-Cross-Ref object which is completely analogous to the BIND-Iid-Cross-Ref object.

Pathway cross-reference data is contained in a BIND-Pid-Cross-Ref object. This object only keeps a list of submitters for each pathway record. Since no other objects can reference a pathway record, the BIND-Pid-Cross-Ref object does not contain references to other records.

The GI/DI cross-reference information is stored in a BIND-Cross-Ref object. This object links a biological sequence to a list of interactions, molecular complexes and pathways that contain it.

PMID/MUID cross-reference data is maintained in a BIND-Pub-Cross-Ref object. This cross-reference scheme is analogous to that of GI/DI accession numbers.

The full cross-reference system allows quick and easy searching of the database by any of the five indexed accession numbers.

Exported Data Types

Typical ASN.1 data specifications make certain data types available for use by other ASN.1 specifications by exporting them. BIND currently exports the top-level data types BIND-Submit, BIND-Interaction, BIND-Interaction-set, BIND-Pathway, BIND-Pathway-set, BIND-Molecular-Complex and BIND-Complex-set.

Flat-file Record Format

Many current biological data specifications are available in a flat-file format for use with simple flat-file databases. Examples include the GenBank flat-file format and the FASTA format for biological sequence representation. BIND can be made available in a flat-file database record format that mirrors the BIND ASN.1 specification. Therefore, BIND may include ASN.1 flat-file conversion software tools.

Data Entry

BIND may rely on the following different sources for data entry.

1. Manual Data Entry:

Data is entered manually via web based forms handled by CGI scripts on a World Wide Web Server. This allows entry of data from individual computers on a users own time, from anywhere in the world. BIND indexers review and validate public entries as they arrive. Researchers can enter their data after they have finished an experiment.

(i) Curated Data entry:

Data that is already present in the literature will be entered into BIND.

(ii) User data entry:

When a paper about protein or DNA sequence or protein structure is about to be published, an author generally obtains an accession number to a database, such as GenBank or PDB. An author of a paper containing information about biomolecular interactions, complexes, or pathway information, will obtain a similar accession number from BIND. A BIND indexer will validate the incoming data and issue an accession number. This follows the GenBank model.

2. Automated Data Entry:

Data gathering agents will gather data from various sources on the Internet. Possible examples include:

A. NCBI's MMDB structure database that contains many protein multimers, with accompanying detailed atomic interaction information.

B. DIP (Database of Interacting Proteins) contains many protein-protein interactions.

C. FlyNets—the drosophila interactome database—contains protein-protein, protein-DNA DNA and protein-RNA interactions.

D. Ligand DB—compound database from Japan.

E. Klotho-another compound database.

3. Data Entry Direct From Experimental Systems:

A separate instance of BIND, a BIND satellite database, can be used as a local repository to store experimental data as it is gathered, but before it is analyzed. Any data that is then used in a publication can then be transferred easily to the public database. A BIND satellite can download the current public database and merge it with local data.

Examples of experiments that can be used to locate interactions include:

A. Immuno-precipitation

B. Affinity chromatography

C. Yeast two hybrid

D. DNA footprinting

E. Reconstitution experiments (using various detection tools such as FRET, hydroxyl radical footprinting, isotope exchange combined with mass spectroscopy, and fluorescence anisotropy)

Accessing BIND Data

BIND can be accessed via a user-friendly Web interface on the Internet and anyone using a current web browser can access BIND data. BIND records may be searchable by Interaction ID (iid), Molecular Complex ID (mcid), Pathway ID (pid), NCBI gi, and PubMed or Medline ID. The data can be text indexed and searchable using keywords. There is a BLAST interface to BIND.

Visualization of BIND data

Web based Java applets that will dynamically represent pathways and molecular complexes have been designed. These form the preferred front end of the BIND system. For example, when a pathway is graphically represented, the image is mouse clickable so that information about the record and other records in the database will be easily accessible.

Implementation

This section gives an overview of the BIND database. The implementation allows data entry and data retrieval supporting the full BIND 1.0 ASN.1 specification. Programmed fully using the C programming language for maximum speed and compatibility, a BIND application programming interface (API) has been written to allow applications to easily use data in the BIND database. The API makes use of two C libraries, the NCBI Toolkit (ftp://ncbi.nlm.nih.gov/toolbox) for ASN.1 handling and more and the CodeBase (http:H/www.sequiter.com/) database library for a database implementation. Using this API, web-based applications have been developed for data entry, retrieval and management. All data is entered and retrieved using web-based forms generated by CGI programs written in C. Interaction data is entered using this web-based user interface.

The BIND database uses the Seqhound database system as a resource. Seqhound is a mirror of GenBank, the NCBI taxonomy database and the PDB (Bernstein et al., 1978) data in NCBI MMDB form (Hogue et al., 1996). Seqhound derived data allows BIND to quickly and easily use sequence, taxonomy and 3D molecular structure information for validation and for information retrieval.

Data visualization and data mining systems have been designed for the database implementation. The spider will traverse BIND searching for new signaling pathways. It will traverse all pathway cross talk links looking for signaling routes that are not present in BIND. The results of this search will be potentially unknown cellular signaling pathways. The proteins of these new pathways can also be examined to see if they contain known binding domains, such as SH2 and SH3 domains, which will increase the likelihood of pathway cross talk. The short list of newly found potential pathways can then be experimentally evaluated.

With the current information garnered by genomic sequencing projects, homologous cell signaling pathways can be found in other organisms by knowing all of the gene products in a pathway in a related organism. Even between non-related organisms, certain 'housekeeping' pathways should not be expected to differ much.

BIND can be used to find networks of biological signaling pathways whose topologies can support signal properties that simple pathways can not. It has been shown that certain kinds of signaling networks have properties that cannot be seen with simple signal pathways. Storing of information, large-scale signal attenuation and signal control are some of these properties. It has been supposed that memory can have a basis in the long term storing of information in certain signaling pathways. (Bjalla, US and Iyengar R, Emergent Properties in Signaling Networks, Science 283(5400): 381–7, Jan. 15, 1999)

BIND can also be used to identify a biomolecular interaction that is similar to a reference biomolecular interaction stored in BIND. The user interface allows the user to initiate a similarity search for each molecule in the test biomolecular interaction. The results can be screened by selected taxonomy. A putative biomolecular interaction is then assembled to create a test record. The BIND database is then examined to match the test record with the records therein to produce a matching record containing a reference biomolecular interaction that matches the test biomolecular interaction.

Examples of a BIND specification are attached as Appendix A and Appendix B.

Having illustrated and described the principles of the invention in a preferred embodiment, it should be appreciated to those skilled in the art that the invention can be modified in arrangement and detail without departure from such principles. We claim all modifications coming within the scope of the following claims.

All publications, patents and patent applications referred to herein are incorporated by reference in their entirety to the same extent as if each individual publication, patent or patent application was specifically and individually indicated to be incorporated by reference in its entirety.

References

Altschul, S. F., Madden, T. L., Schaffer, A. A., Zhang, J., Zhang, Z., Miller, W. & Lipman, D. J. (1997) Gapped BLAST and PSI-BLAST: a new generation of protein database search programs. *Nucleic.Acids.Res.*, 25, 3389–3402.

Bairoch, A. & Apweiler, R. (1999) The SWISS-PROT protein sequence data bank and its supplement TrEMBL in 1999. *Nucleic.Acids.Res.*, 27, 49–54.

Benson, D. A., Boguski, M. S., Lipman, D. J., Ostell, J., Ouellette, B. F., Rapp, B. A. & Wheeler, D. L. (1999) GenBank. *Nucleic.Acids.Res.*, 27, 12–17.

Bernstein, F. C., Koetzle, T. F., Williams, G. J., Meyer, E. F. J., Brice, M. D., Rodgers, J. R., Kennard, O., Shimanouchi, T. & Tasumi, M. (1978) The protein data bank: a computer-based archival file for macromolecular structures. *Arch.Biochem.Biophys.*, 185, 584–591.

DDBJ/EMBL/GenBank. (1997) *The DDBJ/EMBL/GenBank Feature Table Definition Version* 2.1

Eilbeck, K., Brass, A., Paton, N. & Hodgman, C. (*1999*) INTERACT: an object oriented protein-protein interaction database. *Ismb.*, 7, 87–94.

Gasteiger, J. (1996) Chemical Information in 3D-Space. *J.Chem.Inf Comput.Sci.*, 36, 1030–1037.

Higgins, D. G., Thompson, J. D. & Gibson, T. J. (1996) Using CLUSTAL for multiple sequence alignments. *Methods Enzymol.*, 266, 383–402.

Hogue, C. W., Ohkawa, H. & Bryant, S. H. (1996) A dynamic look at structures: WWW-Entrez and the Molecular Modeling Database. *Trends.Biochem.Sci.*, 21, 226–229.

Igarashi, T. & Kaminuma, T. (1997) Development of a cell signaling networks database. *Pac.Symp.Biocomput.*, 187–197.

Kans, J. A. & Ouellette, B. F. (1998) Submitting DNA Sequences to the Databases. In Baxevanis, A. D. & Ouellette, B. F. (eds), Bioinformatics. John Wiley & Sons Toronto pp.319–353.

Marcotte, E. M., Pellegrini, M., Ng, H. L., Rice, D. W., Yeates, T. O. & Eisenberg, D. (1999) Detecting protein function and protein-protein interactions from genome sequences. *Science*, 285, 751–753.

Mendelsohn, A. R. & Brent, R. (1999) Protein interaction methods—toward an end game. *Science*, 284, 1948–1950.

Mohr, E., Horn, F., Janody, F., Sanchez, C., Pillet, V., Bellon, B., Roder, L. & Jacq, B. (1998) FlyNets and GIF-DB, two internet databases for molecular interactions in Drosophila melanogaster. *Nucleic.Acids.Res.*, 26, 89–93.

Object Management Group. (1996) *CORBA Architecture and Specifications*, OMG Publications Ostell, J. & Kans, J. A. (1998) The NCBI Data Model. In Baxevanis, A.D. & Ouellette, B. F. (eds), Bioinformatics. John Wiley & Sons pp.121–144.

Schuler, G. D., Epstein, J. A., Ohkawa, H. & Kans, J. A. (1996) Entrez: molecular biology database and retrieval system. *Methods Enzymol.*, 266, 141–162.

Stoesser, G., Tuli, M. A., Lopez, R. & Sterk, P. (1999) The EMBL Nucleotide Sequence Database. *Nucleic.Acids.Res.*, 27, 18–24.

Sugawara, H., Miyazaki, S., Gojobori, T. & Tateno, Y. (1999) DNA Data Bank of Japan dealing with large-scale data submission. *Nucleic.Acids.Res.*, 27, 25–28.

Weininger, D. (1988) SMILES, a Chemical Language and Information System. *J.Chem.Inf.Comput.Sci.*, 28, 31–36.

What is claimed is:

1. A system for electronically managing, finding, and/or visualizing biomolecular interactions comprising a computer system including at least one computer receiving data on biomolecular interactions from a plurality of providers and processing such data to create and maintain images and/or text defining molecules in biomolecular interactions as connectivity graphs of atoms and bonds in the molecules that can include three-dimensional coordinates, said computer system, in response to data requests, creating and transmitting to a plurality of end-users, the images and/or text defining biomolecular interactions.

2. A system as claimed in claim 1 wherein the biomolecular interactions comprise a protein, nucleic acid, ligand, molecular complex, and signaling pathway.

3. A method for displaying on a computer screen information concerning biomolecular interactions comprising retrieving an image and/or text defining a biomolecular interaction from a system as claimed in claim 1.

4. A data structure stored in the memory of a computer, the data structure having a plurality of records, each record containing a biomolecular interaction; wherein molecules in the biomolecular interaction are defined by connectivity graphs of atoms and bonds in the molecules that can include three-dimensional coordinates, and information relating to the biomolecular interaction.

5. A data structure as claimed in claim 4 wherein the information is accessible by using indices representing selections of information from the connectivity graphs.

6. A method for storing a representation of a biomolecular interaction in a memory of a computer system, the method executed on a computer system and comprising the steps of:
 (a) identifying connectivity graphs of atoms and bonds in molecules of a biomolecular interaction that can include three-dimensional coordinates; and
 (b) storing a record in a data structure as claimed in claim 4.

7. A method for storing a representation of a biomolecular interaction in a memory of a computer system, the method executed on a computer system and comprising the steps of:
 (a) identifying connectivity graphs of atoms and bonds in molecules of a biomolecular interaction that can include three-dimensional coordinates;
 (b) generating one or more indices from information in the connectivity graphs; and
 (c) storing a record in a data structure as claimed in claim 5.

8. A method for identifying a biomolecular interaction that is similar to a reference biomolecular interaction, the method executed on a computer and comprising the steps of:
 (a) conducting a similarity search for each molecular in a test biomolecular interaction;
 (b) screening the results of the similarity search;
 (c) assembling a putative biomolecular interaction to create a test record;
 (d) accessing one or more records in a data structure stored in the memory, the data structure having a plurality of records, each of the records containing a reference biomolecular interaction and information relating to the reference biomolecular interaction wherein molecules of a biomolecular interaction are defined by connectivity graphs of atoms and bonds in the molecules that can include threedimensional coordinates; and
 (e) matching the test record with each record in the data structure to produce a matching record containing a reference biomolecular interaction matching the test biomolecular interaction.

9. A computer system for storing a representation of one or more biomolecular interactions in a memory in the computer system and for comparing one or more reference biomolecular interactions to a test biomolecular interaction, comprising:
 (a) a database means stored in the memory representing one or more biomolecular interactions, each molecule in biomolecular interaction represented by connectivity graphs of atoms and bonds in the molecule that can include threedimensional coordinates; and (b) a data structure means for storing a plurality of record means, each record means containing connectivity graphs of atoms and bonds in molecules of the test biomolecular interaction.

10. A computer system comprising memory means, storage means, program means, and stored means for representing virtual-models of biomolecular interactions in the computer system comprising:

(a) one or more libraries of reference biomolecular interactions that comprise any number of attributes or components of the biomolecular interactions which values are either being used to describe characteristics of the types of biomolecular interactions in the computer system, or values or data structures used by the program at runtime, or are to be used to more specifically describe characteristics of individual components of the biomolecular interaction that each instance of a type of biomolecular interaction is to represent, or characteristics of each instance of a biomolecular interaction in the computer system; wherein the attributes have values of any type in the computer system or in a network accessible by the computer system, wherein the molecules in a biomolecular interaction are defined by connectivity graphs of atoms and bonds in the molecules that can include three-dimensional coordinates;

(b) means for manipulating the biomolecular interaction by domain experts or program means comprising visual means for making the biomolecular interactions available through menus or palettes or programmatic means; and (c) constructor means to create new instances from the definitions of the biomolecular interactions, and means to establish directional output-input links between complementary instances of the biomolecular interactions directly or through components.

11. A computer system comprising:

(a) a database having a plurality of records, each of said records containing a reference biomolecular interaction, wherein molecules in the biomolecular interaction are defined by connectivity graphs of atoms and bonds in the molecules that can include three-dimensional coordinates and descriptive information from an external database which information correlates the biomolecular interactions to records in the external database; and (b) a user interface allowing a user to selectively view information regarding a biomolecular interaction.

12. A computer system as claimed in claim 11 comprising:

(a) a database having a plurality of records, each of said records containing a reference biomolecular interaction, wherein molecules in the biomolecular interaction are defined by connectivity graphs of atoms and bonds in the molecules that can include three-dimensional coordinates and descriptive information from an external database, which information correlates the biomolecular interactions to records in the external database;

(b) a processor in communication with said database and responsive to user input to access records in said database; and (c) a user interface allowing a user to provide user input to said processor to selectively view information regarding a biomolecular interaction.

13. A computer system as claimed in claim 12 wherein the records are encoded by standard data grammars.

14. A computer system as claimed in claim 12 wherein the records are encoded in ASN.1 or XML.

15. A computer system as claimed in claim 12 wherein the user interface further comprises user selectable links to enable a user to access additional information for a biomolecular interaction.

16. A computer system as claimed in claim 15 wherein the links comprise HTML links.

17. A method for presenting information pertaining to records of biomolecular interactions in a computer database, the records containing information identifying the biomolecular interactions and defining molecules in the biomolecular interactions by connectivity graphs of atoms and bonds in the molecules that can include three-dimensional coordinates, the method comprising the steps of:

(a) providing an interface for entering query information relating to a biomolecular interaction;

(b) examining records in said database to locate data corresponding to the entered query information; and (c) displaying the data corresponding to the entered query information.

18. A computer program product comprising a computer-usable medium having computer-readable program code embodied thereon relating to a plurality of records of biomolecular interactions, the records identifying the biomolecular interactions and defining molecules in the biomolecular interactions by connectivity graphs of atoms and bonds in the molecules that can include three-dimensional coordinates, the computer program product comprising computer-readable program code for effecting the following steps within a computing system:

(a) providing an interface for entering query information relating to a biomolecular interaction;

(b) locating data corresponding to the entered query information; and (c) displaying the data corresponding to the entered query information.

19. A database system comprising a plurality of internal records, the database comprising a plurality of records, wherein each record contains a reference biomolecular interaction wherein the molecules in the biomolecular interaction are defined by connectivity graphs of atoms and bonds in the molecules that can include three-dimensional coordinates and descriptive information from an external database which information correlates the biomolecular interactions to records in the external database.

20. A database storing information relating to biomolecular interactions comprising:

(a) first data types describing biomolecular interactions between chemical objects and comprising objects identifying the biomolecular interactions and defining molecules in the biomolecular interactions by connectivity graphs of atoms and bonds in the molecules that can include three-dimensional coordinates;

(b) second data types describing collections of biomolecular interactions; and (c) third data types describing pathways between said collections of interactions.

21. A database as claimed in claim 20 wherein each of said first data types includes objects for said chemical objects, each of said objects including at least one of a pointer to an external database describing the chemical object, a sequence, and connectivity graphs.

22. A database as claimed in claim 21 wherein the first data types are stored as records.

23. A database as claimed in claim 22 wherein the second data types include lists of identifications referencing the biomolecular interactions in said collections.

24. A database as claimed in claim 23 wherein said third data types include objects for said chemical objects that can form networks of interactions.

25. A database as claimed in claim 24 wherein said networks of interactions include metabolic pathways and cell signaling pathways.

26. A database as claimed in claim 25 wherein third data types include sequences of identifications referencing biomolecular interactions that make up said pathways.

* * * * *